(12) United States Patent
Meesapyodsuk et al.

(10) Patent No.: US 8,003,853 B2
(45) Date of Patent: Aug. 23, 2011

(54) FATTY ACID DESATURASES AND USES THEREOF

(75) Inventors: Dauenpen Meesapyodsuk, Saskatoon (CA); Xiao Qiu, Saskatoon (CA)

(73) Assignee: Bioriginal Food & Science Corp., Saskatoon (CA)

( * ) Notice: Subject to any disclaimer, the term of this patent is extended or adjusted under 35 U.S.C. 154(b) by 960 days.

(21) Appl. No.: 11/776,219

(22) Filed: Jul. 11, 2007

(65) Prior Publication Data

US 2008/0072351 A1    Mar. 20, 2008

Related U.S. Application Data

(60) Provisional application No. 60/830,079, filed on Jul. 11, 2006.

(51) Int. Cl.
| | |
|---|---|
| *A01H 5/00* | (2006.01) |
| *C12N 15/82* | (2006.01) |
| *C12N 1/20* | (2006.01) |
| *C12N 5/10* | (2006.01) |
| *C07H 21/04* | (2006.01) |

(52) U.S. Cl. .................... 800/298; 800/281; 435/252.3; 435/419; 536/23.2

(58) Field of Classification Search .......................... None
See application file for complete search history.

(56) References Cited

U.S. PATENT DOCUMENTS

2005/0216975 A1    9/2005    Yadav et al.

FOREIGN PATENT DOCUMENTS

| WO | WO-03/099216 A2 | 12/2003 |
| WO | WO 2005047479 A2 * | 5/2005 |
| WO | WO-2007/147256 A1 | 12/2007 |

OTHER PUBLICATIONS

Sequence alignment of SEQ ID No: 1 with Sequence Accession AEA14784, Damude et al, SEQ ID No: 3, run date May 18, 2010.*
Damude, H. G., et al., "Identification of Bifunctional Δ12/ω3 Fatty Acid Desaturases for Improving the Ratio of ω3 to ω6 Fatty Acids in Microbes and Plants", PNAS, 2006, vol. 103, No, 25, pp. 9446-9451.
"Subname: Full=Delta-12 Fatty Acid Desaturase", EMBL Database, EBI Accession No. Q27ZJ7, Apr. 4, 2006.
Meesapyodsuk, D., et al., "Primary Structure, Regioselectivity, and Evolution of the Membrane-Bound Fatty Acid Desaturases of *Claviceps purpurea*", The Journal of Biological Chemistry, 2007, vol. 282, No. 28, pp. 20191-20199.
Meesapyodsuk, D., et al., "An Oleate Hydroxylase from the Fungus *Claviceps purpurea*: Cloning, Functional Analysis, and Expression in Arabidopsis". Plant Physiology, 2008, vol. 147, pp. 1325-1333.
International Search Report for Application No. PCT/CA2007/001218, dated Oct. 26, 2007.
Written Opinion for Application No. PCT/CA2007/001218, dated Oct. 26, 2007.

\* cited by examiner

*Primary Examiner* — Elizabeth McElwain
(74) *Attorney, Agent, or Firm* — Connolly Bove Lodge & Hutz, LLP

(57) ABSTRACT

The invention provides isolated nucleic acid molecules which encode novel fatty acid desaturase family members. The invention also provides recombinant expression vectors containing desaturase nucleic acid molecules, host cells into which the expression vectors have been introduced, and methods for large-scale production of long chain polyunsaturated fatty acids (LCPUFAs), e.g., SDA, EPA and DHA.

33 Claims, 8 Drawing Sheets

FIGURE 1

Sequences of the Desaturase CpDesX

FIG. 1A (CpDesX nucleotide sequence) (SEQ ID NO:1)

```
ATGGCTGCTACCACTTCTGCAATGTCTAAGGACGCTGTTCTGCGGCGCACTGCGGCCGCAACGACTGCCATCGATCACGA
GTCGTCGACCTCTGCCAGTCCAGCCGACTCGCCTAGACTCTCAGCCTCGTCCACGTCGCTTTCGTCGCTTTCTTCTCTCG
ATGCGAAGGACAAGGACGACGAGTATGCCGGCCTTCTTGACACATACGGAAACGCCTTCACACCCCCCGACTTCACTATC
AAGGACATCCGTGATGCCATACCCAAGCATTGCTTCGAACGCTCTGCCATCAAGGGATACGCATATATTCTTCGCGACGT
CGCCTGTCTTTCTACTACGTTCTACCTGTTCCACAACTTCGTGACGCCCGAGAACGTCCCCTACACTCCCCTTCGTGTCT
TTCTCTGGGGTGTTTACACTGCCCTGCAAGGTCTATTTGGAACTGGACTCTGGATTATTGCCCACGAATGTGGCCACGGC
GCCTTCTCTCCTTCAACCTTGACCAACGACCTTACCGGCTGGGTCCTTCACTCAGCTCTCCTTGTTCCCTATTTCAGCTG
GAAGTTTTCCCACAGTGCGCATCACAAAGGAACTGGAAACATGGAGCGCGACATGGCTTTCCTTCCCCGCACACGTGCGC
AGTATGCCACTCGATTTGGACGTGCGATGGATCAACTTGGTGACCTTTGCGAAGAGACACCCATTTACACGGCTGGGTTC
TTGGTTTTCCAGCAGCTCCTAGGCTGGCCTAGCTATCTTATAGCGAACGTCACAGGTCACGACCTCCACGAACGCCAGCG
TGAGGGTCGAGGTAAGGGCAAGAAGAACGGTTTCGGGGCACCGTAAATCACTTTGATCCCCGCAGCCCTATTTCGATG
ACAAACACGCCAAGTTCATTGTTCTCTCTGACATCGGCCTGGGTCTTGCTATCGCTGCTCTGGTGTATCTTGGCAACCGT
TTCGGCTGGGCTAACGTGGCTGTTTGGTATTTCGTGCCCTATCTTTGGGTGAATCACTGGATCGTTGCCATCACGTTCCT
CCAGCATACGGATCCAACTCTGCCGCATTACACCGCCGAAGAGTGGAACTTTGTTCGCGGTGCCGCTGCTACCATTGATC
GCGAGATGGGCTTCATTGGCCGCCACCTTTTCCATGGCATTGTCGAGACCCATGTCCTCCATCACTATGTCAGCTCTATA
CCGTTCTACAACGCGGACGAAGCCTCCGAGGCCATAAAACCGGTTATGGGCAAGCACTATCGATCTGAAACCAAAGACGG
ACCCATGGGATTTATCCGCGCTCTTTGGAAGACTGCTCGCTGGTGCCAGTGGGTAGAGCCTAGTGCCGATGCGCAAGGTG
CTGGAGAGGGCGTGTTGTTCTTCCGCAACCGAAATGGTCTCGGCACGAAACCCATTTCGATGAGAACTCAGTAG
```

FIG. 1B (CpDesX amino acid sequence) (SEQ ID NO:2)

```
MAATTSAMSKDAVLRRTAAATTAIDHESSTSASPADSPRLSASSTSLSSLSSLDAKDKDDEYAGLLDTYGNAFTPPDFTI
KDIRDAIPKHCFERSAIKGYAYILRDVACLSTTFYLFHNFVTPENVPYTPLRVFLWGVYTALQGLFGTGLWIIAHECGHG
AFSPSTLTNDLTGWVLHSALLVPYFSWKFSHSAHHKGTGNMERDMAFLPRTRAQYATRFGRAMDQLGDLCEETPIYTAGF
LVFQQLLGWPSYLIANVTGHDLHERQREGRGKGKKNGFGGTVNHFDPRSPIFDDKHAKFIVLSDIGLGLAIAALVYLGNR
FGWANVAVWYFVPYLWVNHWIVAITFLQHTDPTLPHYTAEEWNFVRGAAATIDREMGFIGRHLFHGIVETHVLHHYVSSI
PFYNADEASEAIKPVMGKHYRSETKDGPMGFIRALWKTARWCQWVEPSADAQGAGEGVLFFRNRNGLGTKPISMRTQ
```

FIG. 1C
(CpDesX Coding Region)

```
   1    M   A   A   T   T   S   A   M   S   K   D   A   V   L   R   R   T   A   A   A
   1    ATGGCTGCTACCACTTCTGCAATGTCTAAGGACGCTGTTCTGCGGCGCACTGCGGCCGCA
  21    T   T   A   I   D   H   E   S   S   T   S   A   S   P   A   D   S   P   R   L
  61    ACGACTGCCATCGATCACGAGTCGTCGACCTCTGCCAGTCCAGCCGACTCGCCTAGACTC
  41    S   A   S   S   T   S   L   S   S   L   S   S   L   D   A   K   D   K   D   D
 121    TCAGCCTCGTCCACGTCGCTTTCGTCGCTTTCTTCTCGATGCGAAGGACAAGGACGAC
  61    E   Y   A   G   L   L   D   T   Y   G   N   A   F   T   P   P   D   F   T   I
 181    GAGTATGCCGGCCTTCTTGACACATACGGAAACGCCTTCACACCCCCCGACTTCACTATC
  81    K   D   I   R   D   A   I   P   K   H   C   F   E   R   S   A   I   K   G   Y
 241    AAGGACATCCGTGATGCCATACCCAAGCATTGCTTCGAACGCTCTGCCATCAAGGGATAC
 101    A   Y   I   L   R   D   V   A   C   L   S   T   T   F   Y   L   F   H   N   F
 301    GCATATATTCTTCGCGACGTCGCCTGTCTTTCTACTACGTTCTACCTGTTCCACAACTTC
 121    V   T   P   E   N   V   P   Y   T   P   L   R   V   F   L   W   G   V   Y   T
 361    GTGACGCCCGAGAACGTCCCCTACACTCCCCTTCGTGTCTTTCTCTGGGGTGTTTACACT
 141    A   L   Q   G   L   F   G   T   G   L   W   I   I   A   H   E   C   G   H   G
 421    GCCCTGCAAGGTCTATTTGGAACTGGACTCTGGATTATTGCCCACGAATGTGGCCACGGC
 161    A   F   S   P   S   T   L   T   N   D   L   T   G   W   V   L   H   S   A   L
 481    GCCTTCTCTCCTTCAACCTTGACCAACGACCTTACCGGCTGGGTCCTTCACTCAGCTCTC
 181    L   V   P   Y   F   S   W   K   F   S   H   S   A   H   H   K   G   T   G   N
 541    CTTGTTCCCTATTTCAGCTGGAAGTTTTCCCACAGTGCGCATCACAAAGGAACTGGAAAC
 201    M   E   R   D   M   A   F   L   P   R   T   R   A   Q   Y   A   T   R   F   G
 601    ATGGAGCGCGACATGGCTTTCCTTCCCCGCACACGTGCGCAGTATGCCACTCGATTTGGA
 221    R   A   M   D   Q   L   G   D   L   C   E   E   T   P   I   Y   T   A   G   F
 661    CGTGCGATGGATCAACTTGGTGACCTTTGCGAAGAGACACCCATTTACACGGCTGGGTTC
 241    L   V   F   Q   Q   L   L   G   W   P   S   Y   L   I   A   N   V   T   G   H
 721    TTGGTTTTCCAGCAGCTCCTAGGCTGGCCTAGCTATCTTATAGCGAACGTCACAGGTCAC
 261    D   L   H   E   R   Q   R   E   G   R   G   K   G   K   K   N   G   F   G   G
 781    GACCTCCACGAACGCCAGCGTGAGGGTCGAGGTAAGGGCAAGAAGAACGGTTTCGGGGGC
 281    T   V   N   H   F   D   P   R   S   P   I   F   D   D   K   H   A   K   F   I
 841    ACCGTAAATCACTTTGATCCCCGCAGCCCTATTTTCGATGACAAACACGCCAAGTTCATT
 301    V   L   S   D   I   G   L   G   L   A   I   A   A   L   V   Y   L   G   N   R
 901    GTTCTCTCTGACATCGGCCTGGGTCTTGCTATCGCTGCTCTGGTGTATCTTGGCAACCGT
 321    F   G   W   A   N   V   A   V   W   Y   F   V   P   Y   L   W   V   N   H   W
 961    TTCGGCTGGGCTAACGTGGCTGTTTGGTATTTCGTGCCCTATCTTTGGGTGAATCACTGG
 341    I   V   A   I   T   F   L   Q   H   T   D   P   T   L   P   H   Y   T   A   E
1021    ATCGTTGCCATCACGTTCCTCCAGCATACGGATCCAACTCTGCCGCATTACACCGCCGAA
 361    E   W   N   F   V   R   G   A   A   A   T   I   D   R   E   M   G   F   I   G
1081    GAGTGGAACTTTGTTCGCGGTGCCGCTGCTACCATTGATCGCGAGATGGGCTTCATTGGC
 381    R   H   L   F   H   G   I   V   E   T   H   V   L   H   H   Y   V   S   S   I
1141    CGCCACCTTTTCCATGGCATTGTCGAGACCCATGTCCTCCATCACTATGTCAGCTCTATA
 401    P   F   Y   N   A   D   E   A   S   E   A   I   K   P   V   M   G   K   H   Y
1201    CCGTTCTACAACGCGGACGAAGCCTCCGAGGCCATAAAACCGGTTATGGGCAAGCACTAT
 421    R   S   E   T   K   D   G   P   M   G   F   I   R   A   L   W   K   T   A   R
1261    CGATCTGAAACCAAAGACGGACCCATGGGATTTATCCGCGCTCTTTGGAAGACTGCTCGC
 441    W   C   Q   W   V   E   P   S   A   D   A   Q   G   A   G   E   G   V   L   F
1321    TGGTGCCAGTGGGTAGAGCCTAGTGCCGATGCGCAAGGTGCTGGAGAGGGCGTGTTGTTC
 461    F   R   N   R   N   G   L   G   T   K   P   I   S   M   R   T   Q   -
1381    TTCCGCAACCGAAATGGTCTCGGCACGAAACCCATTTCGATGAGAACTCAGTAG
```

FIGURE 2

Sequences of the Desaturase CpDes12

FIG. 2A (CpDes12 nucleotide sequence) (SEQ ID NO:3)

```
ATGGCTGCTGCTACCTCTGCAATGCCAAAGAACTCTGTTCTGCGGCGCACTGCTGCCTCGACGAATGCCAACGACTATGA
GTCGTCGGCCGCTGTCAGTCCAGCCGACTCGCCCAGGCCCTCAGCCTCGTCTACGTCTCTTTCGTCGCTTTCTTCTCTCG
ATGCCAACGACAAGAAAGATGAGTATGCTGGCCTGCTTGACACATACGGAAACGCCTTCACACCCCCCGACTTTACCATC
AAGGACATCCGCGATGCCATTCCCAAGCATTGCTACGAACGCTCTGCCCTCAAAGGCTACGGATACATTCTTCGCGACAT
CGCCTGTCTTTCGACCACGTTCTACCTGTTCCACAACTTCGTAACGCCGGAGAATGTGCCGTCCACTCCCCTTCGATTTG
CGCTCTGGGGTATTTACACTGTCCTGCAAGGTCTTTTTGGAACCGGACTTTGGGTCATTGCCCACGAATGTGGCCATGGT
GCATTTTCTCCGTCCACCCTCATCAACGACGTCACTGGCTGGGTCCTTCACTCAGCTCTCCTCGTTCCTTATTTCAGCTG
GAAGTTTTCCCACAGTGCTCATCACAAGGCCACCGGACATATGGAGCGCGACATGGTTTTTCTTCCCCGAACACGCGCTC
AACAGGCCACCCGACTTGGGCGTGCGGTTGAGGAACTCGGCGATCTTTGCGAGGAGACGCCCATTTACACGGCCCTGCAC
TTGGTAGGCCAACAGCTCATCGGTTGGCCCAGCTACCTCATGGCCAACGTCACGGGACACAATTTCCACGAACGCCAGCG
GGAGGGTCGAGGCAAAGGCAAGAAGAACGGCTTCGGGGGCAGCGTGAATCACTTTGATCCTCGCAGCCCTATTTTCGAAG
CCCGACACGCCAAGTACATTGTTCTCTCTGACATCGGCCTGGGTCTTGCCATCGCCGCTTTGGTATACCTCGGCAACCGG
TTCGGCTGGGCTAACATGGCTGTCTGGTACTTCCTTCCTTATCTCTGGGTGAACCACTGGCTCGTTGCCATTACGTTCCT
CCAGCACACGGACCCAACTCTGCCTCATTACACAGCCGAAGAATGGAACTATGTTCGTGGAGCTGCTGCTACCATTGATC
GCGAGATGGGCTTCATTGGCCGTCACCTTCTCCATGGCATTATTGAGACCCATGTTCTCCACCACTATGTCAGCTCTATT
CCCTTCTACAACGCCGACGAAGCTTCCGAGGCCATCAAGCCAGTCATGGGCAAGCACTATCGATCGGAAACCAAAGACGG
CCCCGTCGGATTCATCCGCGCTCTTTGGAAGACTGCTCGCTGGTGCCAGTGGGTAGAGCCCAGTGCCGAGGCCGAGGGCG
CTGGCAAGGGCGTCTTGTTCTTCCGCAACCGAAACGGTCTGGGTACAAAGCCCATTTCGATGAAGAATTAG
```

FIG. 2B (CpDes12 amino acid sequence) (SEQ ID NO:4)

```
MAAATSAMPKNSVLRRTAASTNANDYESSAAVSPADSPRPSASSTSLSSLSSLDANDKKDEYAGLLDTYGNAFTPPDFTI
KDIRDAIPKHCYERSALKGYGYILRDIACLSTTFYLFHNFVTPENVPSTPLRFALWGIYTVLQGLFGTGLWVIAHECGHG
AFSPSTLINDVTGWVLHSALLVPYFSWKFSHSAHHKATGHMERDMVFLPRTRAQQATRLGRAVEELGDLCEETPIYTALH
LVGQQLIGWPSYLMANVTGHNFHERQREGRGKGKKNGFGGSVNHFDPRSPIFEARHAKYIVLSDIGLGLAIAALVYLGNR
FGWANMAVWYFLPYLWVNHWLVAITFLQHTDPTLPHYTAEEWNYVRGAAATIDREMGFIGRHLLHGIIETHVLHHYVSSI
PFYNADEASEAIKPVMGKHYRSETKDGPVGFIRALWKTARWCQWVEPSAEAEGAGKGVLFFRNRNGLGTKPISMKN
```

FIG. 2C
(CpDes12 Coding Region)

```
  1   M   A   A   A   T   S   A   M   P   K   N   S   V   L   R   R   T   A   A   S
  1   ATGGCTGCTGCTACCTCTGCAATGCCAAAGAACTCTGTTCTGCGGCGCACTGCTGCCTCG

21   T   N   A   N   D   Y   E   S   S   A   A   V   S   P   A   D   S   P   R   P
 61   ACGAATGCCAACGACTATGAGTCGTCGGCCGCTGTCAGTCCAGCCGACTCGCCCAGGCCC

41   S   A   S   S   T   S   L   S   S   L   S   S   L   D   A   N   D   K   K   D
121   TCAGCCTCGTCTACGTCTCTTTCGTCGCTTTCTTCTCTCGATGCCAACGACAAGAAAGAT

61   E   Y   A   G   L   L   D   T   Y   G   N   A   F   T   P   P   D   F   T   I
181   GAGTATGCTGGCCTGCTTGACACATACGGAAACGCCTTCACACCCCCCGACTTTACCATC

81   K   D   I   R   D   A   I   P   K   H   C   Y   E   R   S   A   L   K   G   Y
241   AAGGACATCCGCGATGCCATTCCCAAGCATTGCTACGAACGCTCTGCCCTCAAAGGCTAC

101   G   Y   I   L   R   D   I   A   C   L   S   T   T   F   Y   L   F   H   N   F
301   GGATACATTCTTCGCGACATCGCCTGTCTTTCGACCACGTTCTACCTGTTCCACAACTTC

121   V   T   P   E   N   V   P   S   T   P   L   R   F   A   L   W   G   I   Y   T
361   GTAACGCCGGAGAATGTGCCGTCCACTCCCCTTCGATTGCGCTCTGGGGTATTTACACT

141   V   L   Q   G   L   F   G   T   G   L   W   V   I   A   H   E   C   G   H   G
421   GTCCTGCAAGGTCTTTTTGGAACCGGACTTTGGGTCATTGCCCACGAATGTGGCCATGGT

161   A   F   S   P   S   T   L   I   N   D   V   T   G   W   V   L   H   S   A   L
481   GCATTTTCTCCGTCCACCCTCATCAACGACGTCACTGGCTGGGTCCTTCACTCAGCTCTC

181   L   V   P   Y   F   S   W   K   F   S   H   S   A   H   H   K   A   T   G   H
541   CTCGTTCCTTATTTCAGCTGGAAGTTTTCCCACAGTGCTCATCACAAGGCCACCGGACAT

201   M   E   R   D   M   V   F   L   P   R   T   R   A   Q   Q   A   T   R   L   G
601   ATGGAGCGCGACATGGTTTTTCTTCCCCGAACACGCGCTCAACAGGCCACCCGACTTGGG

221   R   A   V   E   E   L   G   D   L   C   E   E   T   P   I   Y   T   A   L   H
661   CGTGCGGTTGAGGAACTCGGCGATCTTTGCGAGGAGACGCCCATTTACACGGCCCTGCAC

241   L   V   G   Q   Q   L   I   G   W   P   S   Y   L   M   A   N   V   T   G   H
721   TTGGTAGGCCAACAGCTCATCGGTTGGCCCAGCTACCTCATGGCCAACGTCACGGGACAC

261   N   F   H   E   R   Q   R   E   G   R   G   K   G   K   K   N   G   F   G   G
781   AATTTCCACGAACGCCAGCGGGAGGGTCGAGGCAAAGGCAAGAAGAACGGCTTCGGGGGC

281   S   V   N   H   F   D   P   R   S   P   I   F   E   A   R   H   A   K   Y   I
841   AGCGTGAATCACTTTGATCCTCGCAGCCCTATTTTCGAAGCCCGACACGCCAAGTACATT

301   V   L   S   D   I   G   L   G   L   A   I   A   A   L   V   Y   L   G   N   R
901   GTTCTCTCTGACATCGGCCTGGGTCTTGCCATCGCCGCTTTGGTATACCTCGGCAACCGG

321   F   G   W   A   N   M   A   V   W   Y   F   L   P   Y   L   W   V   N   H   W
961   TTCGGCTGGGCTAACATGGCTGTCTGGTACTTCCTTCCTTATCTCTGGGTGAACCACTGG

341   L   V   A   I   T   F   L   Q   H   T   D   P   T   L   P   H   Y   T   A   E
1021  CTCGTTGCCATTACGTTCCTCCAGCACACGGACCCAACTCTGCCTCATTACACAGCCGAA

361   E   W   N   Y   V   R   G   A   A   A   T   I   D   R   E   M   G   F   I   G
1081  GAATGGAACTATGTTCGTGGAGCTGCTGCTACCATTGATCGCGAGATGGGCTTCATTGGC

381   R   H   L   L   H   G   I   I   E   T   H   V   L   H   H   Y   V   S   S   I
1141  CGTCACCTTCTCCATGGCATTATTGAGACCCATGTTCTCCACCACTATGTCAGCTCTATT

401   P   F   Y   N   A   D   E   A   S   E   A   I   K   P   V   M   G   K   H   Y
1201  CCCTTCTACAACGCCGACGAAGCTTCCGAGGCCATCAAGCCAGTCATGGGCAAGCACTAT

421   R   S   E   T   K   D   G   P   V   G   F   I   R   A   L   W   K   T   A   R
1261  CGATCGGAAACCAAAGACGGCCCCGTCGGATTCATCCGCGCTCTTTGGAAGACTGCTCGC

441   W   C   Q   W   V   E   P   S   A   E   A   E   G   A   G   K   G   V   L   F
1321  TGGTGCCAGTGGGTAGAGCCCAGTGCCGAGGCCGAGGGCGCTGGCAAGGGCGTCTTGTTC

461   F   R   N   R   N   G   L   G   T   K   P   I   S   M   K   N   -
1381  TTCCGCAACCGAAACGGTCTGGGTACAAAGCCCATTTCGATGAAGAATTAG
```

FIGURE 3

Alignment of CpDes12, CpDesX and related sequences

Yeast expression of CpDesX

Yeast expression of CpDes12

Expression of CpDesX in plant *Arabidopsis thaliana*

FATTY ACID DESATURASES AND USES THEREOF

RELATED APPLICATIONS

This application claims priority to U.S. Provisional Application No. 60/830,079, filed Jul. 11, 2006, the entire contents of which are hereby incorporated by reference herein.

BACKGROUND OF THE INVENTION

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3) and arachidonic acid (C20:4). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4, 7, 10, 13, 16, 19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032 S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and AA are both $\Delta 5$ essential fatty acids. They form a unique class of food and feed constituents for humans and animals. EPA belongs to the n-3 series with five double bonds in the acyl chain. EPA is found in marine food and is abundant in oily fish from North Atlantic. AA belongs to the n-6 series with four double bonds. The lack of a double bond in the $\omega$-3 position confers on AA different properties than those found in EPA. The eicosanoids produced from AA have strong inflammatory and platelet aggregating properties, whereas those derived from EPA have anti-inflammatory and anti-platelet aggregating properties. AA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by $\Delta 6$ desaturation. Many physiological and pathological conditions such as aging, stress, diabetes, eczema, and some infections have been shown to depress the $\Delta 6$ desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

The predominant sources of GLA are oils from plants such as evening primrose (*Oenothera biennis*), borage (*Borago officinalis* L.), black currant (*Ribes nigrum*), and from microorganisms such as *Mortierella* sp., *Mucor* sp., and *Cyanobacteria*. However, use of these GLA sources is not ideal due to large fluctuations in availability and costs associated with extraction processes.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as GLA, DHA, EPA and AA.

SUMMARY OF THE INVENTION

The present invention is based, at least in part, on the discovery of nucleic acid molecules encoding novel desaturases from *Claviceps purpurea*. In particular, the *Claviceps purpurea* CpDesX desaturase and CpDes12 desaturase have been identified. Each of these desaturases are capable of introducing double bonds in fatty acids, for example, by desaturating the fatty acids at the $\Delta^{12}$, $\Delta^{15}$ and $\omega^3$ positions. For example, the expression of the CpDesX desaturase in *Saccharomyces cerevisae* has been found to result in the introduction of a $\omega 3$ double bond into linoleic acid (LA) 18:2 (9,12), gamma-linolenic acid (GLA) 18:3 (6,9,12), dihomo-gamma linoleic acid (DGLA) 20:3 (8,11,14), arachidonic acid (AA) 20:4 (5,8,11,14) and eicosadienoic acid 20:2 (11, 14) thereby converting these $\omega^6$ polyunsaturated fatty acids into their $\omega^3$ counterparts. In addition, expression of the CpDesX desaturase in *Saccharomyces cerevisae* has been found to result in the introduction of a Δ12 double bond into 16:1(9) and 18:1(9) forming 16:2(9,12) and 18:2(9,12), respectively. Moreover, expression of the CpDesX desaturase further results in the introduction of a Δ15 double bond into 16:2(9,12) and 18:2(9,12) forming 16:3(9,12,15) and 18:3(9,12,15), respectively.

The use of the nucleic acid molecules and polypeptides of the present invention provides a means for modulating, for example, enhancing, the production of desired unsaturated fatty acids. For example, the introduction of these desaturase nucleic acid and polypeptide molecules in microbial and plant cells, for example, under the control of a seed-specific promoter, will allow for the enhanced production of unsaturated fatty acids in oilseeds, such as GLA 18:3 (6,9,12), ALA 18:3 (9,12,15), SDA 18:4 (6,9,12,15), AA 20:4 (5,8,11,14), EPA 20:5 (5,8,11,14,17), DPA 22:5 (4,7,10,13,16), DHA 22:6 (4,7,10,13,16,19), 20:4 (8,11,14,17), 16:2 (9,12), 18:2 (9,12) and 16:3 (9,12,15).

Accordingly, in one aspect, the present invention is directed to an isolated nucleic acid molecule selected from the group consisting of a) an isolated nucleic acid molecule encoding a fatty acid desaturase from the genus *Claviceps*, or a complement thereof; b) an isolated nucleic acid molecule including the nucleotide sequence of SEQ ID NO: 1 or 3, or a complement thereof; c) an isolated nucleic acid molecule which encodes a polypeptide including the amino acid sequence of SEQ ID NO:2 or 4, or a complement thereof; d) an isolated nucleic acid molecule which encodes a naturally occurring allelic variant of a polypeptide including the amino acid sequence of SEQ ID NO:2 or 4, or a complement thereof; e) an isolated nucleic acid molecule including a nucleotide sequence which is at least 50% identical to the entire nucleotide sequence of SEQ ID NO: 1 or 3, or a complement thereof; f) an isolated nucleic acid molecule including a nucleotide sequence which hybridizes to the complement of the nucleotide sequence of SEQ ID NO: 1 or 3 under stringent conditions, or a complement thereof; g) an isolated nucleic acid molecule including a fragment of at least 15 contiguous nucleotides of the entire nucleotide sequence of SEQ ID NO: 1 or 3, or a complement thereof. In a particular embodiment, the nucleic acid molecule encodes a fatty acid desaturase protein having an activity of catalyzing the introduction of a double bond in a fatty acid, for example at position ω3, Δ12 or Δ15 of the fatty acid and h) an isolated nucleic acid molecule which hybridizes to the complement of the nucleotide sequence of SEQ ID NO:1 or SEQ ID NO:3 in 6× sodium chloride/sodium citrate (SSC) at 65° C., or a complement thereof. In another embodiment, the isolated nucleic acid molecule further includes a nucleotide sequence encoding a heterologous polypeptide.

In another aspect, the invention is directed to a vector, for example, an expression vector, including a nucleic acid molecule of the invention. In a particular embodiment, the nucleic acid molecule may be under the control of a seed-specific promoter, for example, Conlinin 1, Conlinin 2, napin and LuFad3.

In another aspect, the invention is directed to a host cell transfected with the expression vector including a nucleic acid molecule of the invention. The host cell may be a plant cell, for example, a plant cell from an oilseed crop, including, but not limited to, flax (*Linum* sp.), rapeseed (*Brassica* sp.), soybean (Glycine and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*. Alternatively, the host cell may be a microbial cell, including, but not limited to *Candida, Cryptococcus, Lipomyces, Rhodosporidium, Yarrowia, Thraustochytrium, Pythium, Schizochytrium* and *Crythecodinium*.

In another aspect, the invention provides a method of producing a polypeptide by culturing a host cell of the invention in an appropriate culture medium to, thereby, produce the polypeptide, for example, a fatty acid desaturase.

In yet another aspect, the invention provides isolated polypeptides selected from the group consisting of a) an isolated fatty acid desaturase polypeptide from *Claviceps*; b) an isolated polypeptide including the amino acid sequence of SEQ ID NO:2 or 4; c) an isolated polypeptide including a naturally occurring allelic variant of a polypeptide including the amino acid sequence of SEQ ID NO:2 or 4; d) an isolated polypeptide including an amino acid sequence encoded by a nucleic acid molecule including the nucleotide sequence of SEQ ID NO:1 or 3; e) an isolated polypeptide which is encoded by a nucleic acid molecule including the nucleotide sequence which is at least 50% identical to the entire nucleotide sequence of SEQ ID NO:1 or 3; f) an isolated polypeptide including an amino acid sequence which is at least 50% identical to the entire amino acid sequence of SEQ ID NO:2 or 4; and g) an isolated polypeptide including a fragment of a polypeptide including the amino acid sequence of SEQ ID NO:2 or 4, wherein the polypeptide fragment maintains a biological activity of the complete polypeptide. In a particular embodiment, the polypeptide is involved in the production of an unsaturated fatty acid. In another embodiment, the polypeptide catalyzes the formation of a double bond at position ω3, Δ12 or Δ15 of a fatty acid. In another embodiment, the polypeptide also includes a heterologous amino acid sequence.

In another aspect, the invention provides a method for producing an unsaturated fatty acid by culturing a host cell of the invention such that the unsaturated fatty acid is produced. In another aspect, the invention provides a method for producing an unsaturated fatty acid by contacting a composition including at least one desaturase target molecule with at least one polypeptide of the invention under conditions such that the unsaturated fatty acid is produced. In yet another aspect, the invention provides a method of producing a cell capable of generating an unsaturated fatty acid by introducing into the cell a nucleic acid molecule of the invention, wherein the nucleic acid molecule encodes a desaturase having an activity of catalyzing the introduction of a double bond in a fatty acid. In yet another aspect, the present invention is directed to a method of modulating, for example, enhancing, the production of a unsaturated fatty acid by culturing a cell transformed with the expression vector of the invention, such that modulation of the production of the unsaturated fatty acid occurs. In a further aspect, the present invention is directed to a method for the large scale production of an unsaturated fatty acid by culturing a cell transformed with the expression vector of the invention. In certain embodiments, the expression of the nucleic acid molecule results in the modulation of the production of an unsaturated fatty acid including, but not limited to GLA 18:3 (6,9,12), ALA 18:3 (9,12,15), SDA 18:4 (6,9,12,15), AA 20:4 (5,8,11,14), EPA 20:5 (5,8,11,14,17), DPA 22:5 (4,7,10,13,16), DHA 22:6 (4,7,10,13,16,19), 20:4 (8,11,14,17), 16:2 (9,12), 18:2 (9,12) and 16:3 (9,12,15).

In one embodiment, the fatty acid produced by the foregoing methods may be recovered from the culture. In another embodiment, the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacao*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*. In a particular embodiment, the cell is *Brassica juncea*. In yet another embodiment, the cell is a microbial cell, for example, *Candida, Cryptococcus, Lipomyces, Rhodosporidium, Yarrowia, Thraustochytrium, Pythium, Schizochytrium* and *Crythecodinium*.

In yet another aspect, the present invention is directed to a host cell having a) a nucleic acid molecule including the nucleotide sequence of SEQ ID NO: 1 or 3, wherein the nucleic acid molecule is disrupted by at least one technique selected from the group consisting of a point mutation, a truncation, an inversion, a deletion, an addition, a substitution and homologous recombination, for example, such that the fatty acid desaturase activity is disrupted; b) a nucleic acid molecule having the nucleotide sequence of SEQ ID NO: 1 or 3, wherein the nucleic acid molecule includes one or more nucleic acid modifications as compared to the sequence set forth in SEQ ID NO:1, wherein the modification is selected from the group consisting of a point mutation, a truncation, an inversion, a deletion, an addition and a substitution, for example, such that the modified nucleic acid molecule encodes a polypeptide retaining fatty acid desaturase activity; or c) a nucleic acid molecule having the nucleotide sequence of SEQ ID NO:1, wherein the regulatory region of the nucleic acid molecule is modified relative to the wild-type regulatory region of the molecule by at least one technique selected from the group consisting of a point mutation, a truncation, an inversion, a deletion, an addition, a substitution and homologous recombination, for example, so as to modify (e.g., enhance) fatty acid desaturase expression and/or activity.

In other aspects, the invention is directed to a plant including a vector described herein, and oils or seeds produced by the plant. In another aspect, the invention is directed to a composition including the oil and/or seed, wherein the composition is for use as animal feed, a dietary supplement or food. In another aspect, the invention is directed to a pharmaceutical composition comprising the seed or oil. In yet another aspect, the invention is directed to an unsaturated fatty acid obtained by a method described herein. In a further aspect, the invention is directed to compositions including the unsaturated fatty acids produced by a method described herein, wherein the composition is for use as animal feed, a dietary supplement, or food. In yet another aspect, the invention is directed to a pharmaceutical composition including the unsaturated fatty acids produced by a method described herein. In another aspect, the invention is directed to a composition comprising the polypeptides of the invention or the transgenic cells of the invention, for example, for use as animal feed, a dietary supplement, food or a pharmaceutical composition.

Other features and advantages of the invention will be apparent from the following detailed description and claims.

BRIEF DESCRIPTION OF THE DRAWINGS

FIG. 1 shows the nucleotide and amino acid sequence of a desaturase from *Claviceps purpurea* (CpDesX) as follows: the cDNA sequence of the open reading frame (SEQ ID NO:1) (FIG. 1A); the translated amino acid sequence (SEQ ID NO:2) (FIG. 1B) and the cDNA aligned with the translated amino acid sequence (FIG. 1C).

FIG. 2 shows the nucleotide and amino acid sequence of a desaturase from *Claviceps purpurea* (CpDes12) as follows: the cDNA sequence of the open reading frame (SEQ ID NO:3) (FIG. 2A); the translated amino acid sequence (SEQ ID NO:4) (FIG. 2B) and the cDNA aligned with the translated amino acid sequence (FIG. 2C).

FIG. 3 shows an alignment of the amino acid of desaturases from *Claviceps purpurea* (CpDesX (SEQ ID NO: 2) and CpDes12 (SEQ ID NO: 4)) versus that of other fatty acid desaturases and related enzymes including those from *Aspergillus nidulans* (AnOdeA) (SEQ ID NO: 6) and *Arabidopsis* D12-desaturase (AtFAD2) (SEQ ID NO: 5).

DETAILED DESCRIPTION OF THE INVENTION

Figures 4, 4A, 4B:
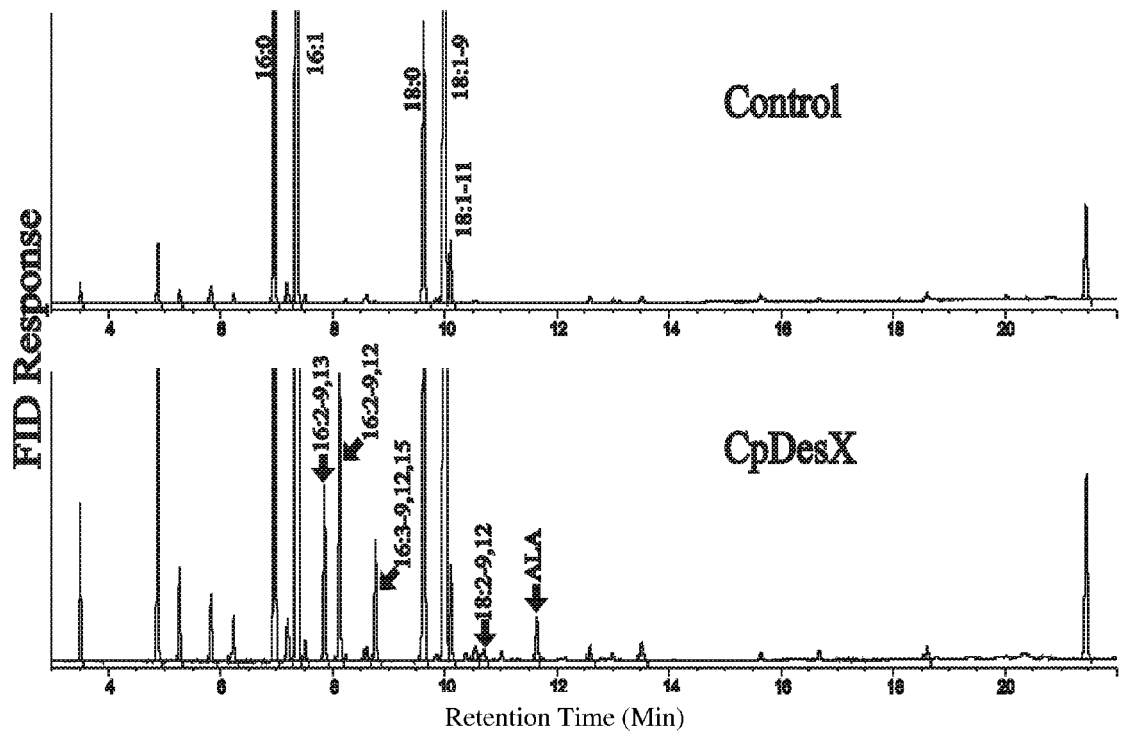
FIG. 4B is a gas chromatographic (GC) analysis of the expression of fatty acids in an experimental strain of yeast transformed with CpDesX as compared to a control strain of yeast (FIG. 4A). The peaks 16:2 (9,13), 16:2 (9,12), 16:3 (9,12,15), 18:2(9,12) and 18:3 (9,12,15) (depicted as ALA) represent the presence of unsaturated fatty acids unique to the yeast strain transformed with CpDesX.

The present invention is based, at least in part, on the discovery of fatty acid desaturases, referred to interchangeably herein as "desaturases" or "desaturase" nucleic acid and protein molecules (e.g., CpDesX and CpDes12 from *Claviceps purpurea* (*C. purpurea*)). These novel molecules are members of the fatty acid desaturase family and are expressed in LCPUFA-producing organisms such as *Claviceps purpurea*, a fungal pathogen which parasitizes young flowers of many grasses. The present invention is further based, at least in part, on the discovery that the *Claviceps purpurea* fatty acid desaturases (e.g., CpDesX and CpDes12) catalyze the introduction of a double bond in a fatty acid. Moreover, the present invention is based, in part, on the discovery that the *Claviceps purpurea* fatty acid desaturases (e.g., CpDesX and CpDes12) are capable of introducing a double bond at multiple positions along a fatty acid chain.

In a particular embodiment, the present invention is directed to a CpDesX desaturase capable of catalyzing a double bond at any of position $\omega 3$, $\Delta 12$ or $\Delta 15$ of a fatty acid. For example, CpDesX catalyzes the introduction of a $\omega 3$ double bond into fatty acids, including, but not limited to, linoleic acid (LA, 18:2(9,12)), gamma-linoleic acid (GLA, 18:3(6,9,12)), dihomo-gamma-linoleic acid (DGLA, 20:3(8, 11,14)), arachidonic acid (AA, 20:4(5,8,11,14)) and eicosadienoic acid (EDA, 20:2 (11, 14)) converting these $\omega^3$ polyunsaturated fatty acids into their $\omega^3$ counterparts; a $\Delta 12$ double bond into, for example, 16:1(9) and 18:1(9) forming 16:2(9,12) and 18:2(9,12), respectively; and a $\Delta 15$ double bond into, for example, 16:2(9,12) and 18:2(9,12) forming 16:3(9,12,15) and 18:3(9,12,15), respectively.

The nucleotide sequence of the isolated *Claviceps purpurea* DesX desaturase, CpDesX, cDNA and the predicted amino acid sequence encoded by the CpDesX cDNA are shown in FIG. 1 as SEQ ID NOs: 1 and 2, respectively. The *Claviceps purpurea* DesX (the open reading frame), which is approximately 1434 nucleotides in length, encodes a protein having a molecular weight of approximately 53.1 kD and which is approximately 477 amino acid residues in length.

In another embodiment, the present invention is directed to a CpDes12 desaturase capable of catalyzing a double bond at position Δ12 of a fatty acid. For example, CpDes12 catalyzes the introduction of a double bond at position Δ12 of fatty acids, such as 16:1(9) and 18:1(9), thereby forming 16:2(9,12) and 18:2(9,12), respectively.

The nucleotide sequence of the *Claviceps purpurea* Des 12 desaturase, CpDes12, cDNA and the predicted amino acid sequence encoded by the CpDes12 cDNA are shown in FIG. 2 as SEQ ID NOs:3 and 4, respectively. The *Claviceps purpurea* Des 12 gene, which is approximately 1431 nucleotides in length, encodes a protein having a molecular weight of approximately 53 kD and which is approximately 476 amino acid residues in length.

Generally, the controlling steps in the production of unsaturated fatty acids, i.e., the unsaturated fatty acid biosynthetic pathway, are catalyzed by membrane-associated fatty acid desaturases, e.g., CpDesX and CpDes12. Specifically, such enzymes catalyze the formation of double bonds between the carbon atoms of a fatty acid molecule. As used herein, the term "unsaturated fatty acid biosynthetic pathway" refers to a series of chemical reactions leading to the synthesis of an unsaturated fatty acid either in vivo or in vitro. Such a pathway includes a series of desaturation and elongation steps which generate unsaturated fatty acids and ultimately, long chain polyunsaturated fatty acids. Such unsaturated fatty acids can include, but are not limited to, gamma linolenic acid (GLA 18:3 (6,9,12)), alpha linolenic acid (ALA 18:3 (9,12,15)), stearidonic acid (SDA 18:4 (6,9,12,15)), arachidonic acid (AA 20:4 (5,8,11,14)), eicosapentaenoic acid (EPA 20:5 (5,8,11,14,17)), docosapentaenoic acid (DPA 22:5 (4,7,10,13,16)), docosahexaenoic acid (DHA 22:6 (4,7,10,13,16,19)), 20:4 (8,11,14,17), 16:2 (9,12), linoleic acid (LA 18:2 (9,12)) and 16:3 (9,12,15).

In view of the involvement of unsaturated fatty acids in various cellular processes including, but not limited to, forming the cellular membranes of various tissues and organelles in mammals (for example, nerve, retina, brain and immune cells), promoting the growth and development of the brain in infants, maintaining normal brain function in adults, affecting photoreceptor function, affecting the signal transduction process, activating rhodopsin, and developing rods and cones, the desaturases of the present invention can be used in the treatment of certain disorders, for example, those disorders characterized by aberrantly regulated growth, proliferation, or differentiation. For example, the desaturases of the present invention can be used in the treatment of diseases such as hypertension, diabetes, hypercholesterolemia, arthritis, atherosclerosis, depression, thrombosis, cancers (e.g., carcinoma, sarcoma, or leukemia), tumor angiogenesis and metastasis, skeletal dysplasia, hepatic disorders, myelodysplastic syndromes, atopic eczema, premenstrual syndrome, and hematopoietic, inflammatory and/or myeloproliferative disorders. Other disorders which may be treated by the methods and compositions of the present invention include, those disorders related to angiogenesis including, but not limited to, hereditary hemorrhagic telangiectasia type 1, fibrodysplasia ossificans progressive, idiopathic pulmonary fibrosis, and Klippel-Trenaunay-Weber syndrome.

As used herein, the term "fatty acid" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18) and which may be saturated or unsaturated. "Unsaturated" fatty acids contain cis double bonds between the carbon atoms. Unsaturated fatty acids encompassed by the present invention include, for example, DHA, GLA, ALA and SDA. "Polyunsaturated" fatty acids contain more than one double bond, often arranged in a methylene interrupted system ($-CH=CH-CH_2-CH=CH-$).

Fatty acids are described herein by a numbering system in which the number before the colon indicates the number of carbon atoms in the fatty acid. In the case of unsaturated fatty acids, the number after the colon is the number of double bonds that are present followed by a number in parentheses that indicates the position of the double bonds. Each number in parenthesis is the lower numbered carbon atom of the two connected by the double bond. For example, oleic acid can be described as 18:1(9) and linoleic acid can be described as 18:2(9,12) indicating 18 carbons, one double bond at carbon 9 and two double bonds at carbons 9 and 12, respectively. Furthermore, the use of a "c" denotes a cis double bond, whereas the use of a "t" denotes a trans double bond.

The term "family" when referring to the protein and nucleic acid molecules of the present invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

For example, members of the desaturase family of proteins may include one, two, or preferably, about three histidine motifs. As used herein, the term "histidine motif" includes a protein domain having at least about two histidine amino acid residues, preferably about three histidine amino acid residues, and is typically found in microsomal desaturases. Examples of histidine motifs include amino acid residues 155-159 (HECGH) (SEQ ID NO: 18), 191-195 (HXXHH) and 391-395 (HVXHH) (SEQ ID NO: 19) of SEQ ID NO:2 and SEQ ID NO:4, encoded by nucleotide residues 463-477, 571-585 and 1171-1185, respectively, of SEQ ID NO:1 and SEQ ID NO:3.

As used interchangeably herein, a "desaturase activity," "biological activity of a desaturase," or "functional activity of a desaturase" includes an activity exerted or mediated by a desaturase protein, polypeptide or nucleic acid molecule on a desaturase responsive cell or on a desaturase substrate, as determined in vivo or in vitro, according to standard techniques. In one embodiment, a desaturase activity is a direct activity such as an association with a desaturase target molecule. In another embodiment, a desaturase direct activity also includes the formation of a double bond between the carbon atoms of a fatty acid molecule to form an unsaturated fatty acid molecule. For purposes of the present invention, the desaturase may introduce a double bond to an entirely saturated fatty acid or, alternatively, may introduce an additional double bond to a previously unsaturated fatty acid.

As used herein, a "target molecule" or "binding partner" is a molecule, for example, a molecule involved in the synthesis of unsaturated fatty acids, for example, an intermediate fatty acid (such as an unsaturated fatty acid on which the incorporation of a further double bond is desired) or a saturated fatty acid, with which a desaturase protein binds or interacts in nature such that a desaturase-mediated function is achieved. In particular embodiments, the target molecule or binding partner may be any of LA 18:2 (9,12), GLA 18:3 (6,9,12), DGLA 20:3 (8,11,14), AA 20:4 (5,8,11,14), eicosadienoic acid 20:2 (11,14), 16:1 (9), 16:2 (9,12), 18:1 (9) and 18:2 (9,12).

Various aspects of the invention are described in further detail in the following subsections:

I. Isolated Nucleic Acid Molecules

One aspect of the invention pertains to isolated nucleic acid molecules that encode desaturase proteins or biologically active portions thereof. In another aspect, the invention is directed to nucleic acid fragments sufficient for use as hybridization probes to identify desaturase-encoding nucleic acid molecules (e.g., desaturase mRNA) and fragments for use as PCR primers for the amplification or mutation of desaturase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated desaturase nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1 or 3, or a portion thereof, can be isolated using standard molecular biology techniques and the sequence information provided herein. Using all or a portion of the nucleic acid sequence of SEQ ID NO: 1 or 3 as hybridization probes, desaturase nucleic acid molecules can be isolated using standard hybridization and cloning techniques (e.g., as described in Sambrook, J. et al. *Molecular Cloning: A Laboratory Manual.* 2$^{nd}$, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 or 3, can be isolated by the polymerase chain reaction (PCR) using synthetic oligonucleotide primers designed based on the sequence of SEQ ID NO:1 or 3.

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to desaturase nucleotide sequences can be prepared by standard synthetic techniques, e.g., using an automated DNA synthesizer.

In still another embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO: 1 or 3 is one which is sufficiently complementary to the nucleotide sequence shown in SEQ ID NO: 1 or 3, such that it can hybridize to the nucleotide sequence shown in SEQ ID NO: 1 or 3, thereby forming a stable duplex. In a particular embodiment, the complementary sequence of the invention are exact complements of the nucleic acid molecules of the invention, for example, a nucleotide sequence of SEQ ID NO: 1 or 3, a nucleotide sequence encoding a polypeptide of SEQ ID NO:2 or 4, an allelic variant thereof, and a nucleotide sequence of at least 70% identity to the nucleotide sequence of SEQ ID NO:1 or 3. For example, the complement may be a full and complete complement of a nucleic acid molecule of the invention, for example, the nucleotide sequence of SEQ ID NO: 1.

In still another embodiment, an isolated nucleic acid molecule of the present invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, 90%, 91%, 92%, 93%, or 94%, and even more preferably at least about 95%, 96%, 97%, 98%, 99% or more identical to the nucleotide sequence shown in SEQ ID NO: 1 or 3 (e.g., to the entire length of the nucleotide sequence), or a portion or complement of any of these nucleotide sequences. Ranges and identity values intermediate to the above-recited ranges (e.g., 70-90% identical or 80-95% identical) are also intended to be encompassed by the present invention. For example, ranges of identity values using a combination of any of the above values recited as upper and/or lower limits are intended to be included.

Moreover, the nucleic acid molecule of the invention can comprise only a portion of the nucleic acid sequence of SEQ ID NO: 1 or 3, for example, a fragment which can be used as a probe or primer or a fragment encoding a portion of a desaturase protein, e.g., a biologically active portion of a desaturase protein. The nucleotide sequence determined from the cloning of the desaturase gene allows for the generation of probes and primers designed for use in identifying and/or cloning other desaturase family members, as well as desaturase homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, of an anti-sense sequence of SEQ ID NO:1 or 3, or of a naturally occurring allelic variant or mutant of SEQ ID NO:1 or 3.

Exemplary probes or primers are at least (or no greater than) 5, 6, 7, 8, 9, 10, 11, 12, 13, 14, 15, 16, 17, 18, 19, 20, 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the desaturase nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment, a set of primers is provided, e.g., primers suitable for use in a PCR, which can be used to amplify a selected region of a desaturase sequence, e.g., a domain, region, site or other sequence described herein. The primers should be at least 5, 6, 7, 8, 9, 10, 11, 12, 13, 14, 15, 16, 17, 18, 19, 20, 25, 30, 35, 40, 45 or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a desaturase protein, such as by measuring a level of a desaturase-encoding nucleic acid in a sample of cells from a subject, e.g., detecting desaturase mRNA levels or determining whether a genomic desaturase gene has been mutated or deleted.

A nucleic acid fragment encoding a "biologically active portion of a desaturase protein" can be prepared by isolating a portion of the nucleotide sequence of SEQ ID NO: 1 or 3, which encodes a polypeptide having a desaturase biological activity (the biological activities of the desaturase proteins are described herein), expressing the encoded portion of the desaturase protein (e.g., by recombinant expression in vitro) and assessing the activity of the encoded portion of the desaturase protein. In an exemplary embodiment, the nucleic acid molecule is at least 10, 15, 20, 25, 30, 35, 40, 45, 50, 100, 150, 200, 250, 300, 350, 400, 450, 500, 550, 600, 650, 700, 750, 1000, 1250, 1300, 1350 or 1400 or more nucleotides in length and encodes a protein having a desaturase activity (as described herein).

The invention further encompasses nucleic acid molecules that differ from the nucleotide sequence shown in SEQ ID NO: 1 or 3 due to degeneracy of the genetic code and thus encode the same desaturase proteins as those encoded by the nucleotide sequence shown in SEQ ID NO:1 or 3. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2 or 4. In yet another embodiment, the nucleic acid molecule encodes the amino acid sequence of human desaturase. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the desaturase proteins. Such genetic polymorphism in the desaturase genes may exist among individuals within a population due to natural allelic variation.

As used herein, the terms "gene" and "recombinant gene" refer to nucleic acid molecules which include an open reading frame encoding a desaturase protein, e.g., oilseed desaturase protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2 or 4. Moreover, the nucleic acid molecule may hybridize to a complement of a nucleic acid molecule comprising SEQ ID NO: 1 or 3, for example, under stringent hybridization conditions.

In addition to the *C. purpurea* fatty acid desaturase of SEQ ID NO: 1 or 3, it will be appreciated by those of ordinary skill in the art that DNA sequence polymorphisms that lead to changes in the amino acid sequences of desaturase proteins may exist within a population (e.g., the *C. purpurea* population). Such genetic polymorphism in the fatty acid desaturase gene may exist among individuals within a population due to natural variation. Such natural variations can typically result in 1-5% variance in the nucleotide sequence of the desaturase gene. Allelic variants of the CpDesX and CpDes12 desaturase include both functional and non-functional desaturase proteins. Functional allelic variants are naturally occurring amino acid sequence variants of the desaturase protein that maintains the ability to, for example, (i) interact with a desaturase substrate or target molecule (for example, a fatty acid such as a saturated fatty acid or an intermediate fatty acid); and/or (ii) form a double bond in a desaturase substrate or target molecule. Functional allelic variants will typically contain only a conservative substitution of one or more amino acids of SEQ ID NO:2 or 4, or a substitution, deletion or insertion of non-critical residues in non-critical regions of the protein.

Non-functional allelic variants are naturally occurring amino acid sequence variants of the desaturase protein, e.g., CpDesX and CpDes12, that do not have the ability to, e.g., (i) interact with a desaturase substrate or target molecule (e.g., an intermediate fatty acid; and/or (ii) form a double bond between carbon atoms in a desaturase substrate or target molecule. Non-functional allelic variants will typically contain a non-conservative substitution, a deletion, or insertion, or premature truncation of the amino acid sequence of SEQ ID NO:2 or 4, or a substitution, insertion, or deletion in critical residues or critical regions of the protein.

The present invention further provides orthologues (e.g., human orthologues of the desaturase proteins). Orthologues of the *C. purpurea* desaturase proteins are proteins that are isolated from other organisms and possess the same desaturase substrate or target molecule binding mechanisms, double bond forming mechanisms, modulating mechanisms of growth and development of the brain in infants, maintenance mechanisms of normal brain function in adults, ability to affect photoreceptor function involved in the signal transduction process, ability to affect rhodopsin activation, development mechanisms of rods and/or cones, and/or modulating mechanisms of cellular growth and/or proliferation of the non-human desaturase proteins. Orthologues of the *C. purpurea* desaturase proteins can readily be identified as comprising an amino acid sequence that is substantially homologous to SEQ ID NO:2 or 4.

Moreover, nucleic acid molecules encoding other desaturase family members and, thus, which have a nucleotide sequence which differs from the desaturase sequences of SEQ ID NO: 1 or 3 are intended to be within the scope of the invention. For example, another desaturase cDNA can be identified based on the nucleotide sequence of CpDesX or CpDes12. Moreover, nucleic acid molecules encoding desaturase proteins from different species, and which, thus, have a nucleotide sequence which differs from the desaturase sequences of SEQ ID NO: 1 or 3 are intended to be within the scope of the invention. For example, *Schizochytrium* or *Crythecodinium* desaturase cDNA can be identified based on the nucleotide sequence of a CpDesX or CpDes12.

Nucleic acid molecules corresponding to natural allelic variants and homologues of the desaturase cDNAs of the invention can be isolated based on their homology to the desaturase nucleic acids disclosed herein using the cDNAs disclosed herein, or a portion thereof, as a hybridization probe according to standard hybridization techniques under stringent hybridization conditions.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 10, 11, 12, 13, 14, 15, 16, 17, 18, 19, 20, 25, 30 or more nucleotides in length and hybridizes under stringent conditions to the nucleic acid molecule comprising the nucleotide sequence of SEQ ID NO:1 or 3. In other embodiment, the nucleic acid is at least 50, 100, 150, 200, 250, 300, 350, 400, 450, 500, 550, 600, 650, 700, 750, 1000, 1250, 1300, 1350 or 1400 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C. or alternatively hybridization in 6×SSC at 65° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2×SSC, 1% SDS.

Preferably, an isolated nucleic acid molecule of the invention that hybridizes under stringent conditions to the sequence of SEQ ID NO: 1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the desaturase sequences that may exist in the population, the skilled artisan will further appreciate that changes can be introduced by mutation into the nucleotide sequences of SEQ ID NO:1 or 3, thereby leading to changes in the amino acid sequence of the encoded desaturase proteins, without altering the functional ability of the desaturase proteins. For example, nucleotide substitutions leading to amino acid substitutions at "non-essential" amino acid residues can be made in the sequence of SEQ ID NO: 1 or 3. A "non-essential" amino acid residue is a residue that can be altered from the wild-type sequence of CpDesX or CpDes12 (e.g., the sequence of SEQ ID NO:2 or 4) without altering the biological activity, whereas an "essential" amino acid residue is required for biological activity. For example, amino acid residues that are conserved among the desaturase proteins of the present invention, e.g., those present in a heme-binding motif or a histidine motif, are predicted to be particularly unamenable to alteration. Furthermore, additional amino acid residues that are conserved between the desaturase proteins of the present invention and other members of the fatty acid desaturase family are not likely to be amenable to alteration.

Accordingly, another aspect of the invention pertains to nucleic acid molecules encoding desaturase proteins that contain changes in amino acid residues that are not essential for activity. Such desaturase proteins differ in amino acid sequence from SEQ ID NO:2 or 4, yet retain biological activity. In one embodiment, the isolated nucleic acid molecule comprises a nucleotide sequence encoding a protein, wherein the protein comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, and even more preferably at least about 95%, 96%, 97%, 98%, 99% or more identical to SEQ ID NO:2 or 4, e.g., to the entire length of SEQ ID NO:2 or 4.

An isolated nucleic acid molecule encoding a desaturase protein homologous to the protein of SEQ ID NO:2 or 4 can be created by introducing one or more nucleotide substitutions, additions or deletions into the nucleotide sequence of SEQ ID NO: 1 or 3, such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a desaturase protein is preferably replaced with another amino acid residue from the same side chain family. Alternatively, in another embodiment, mutations can be introduced randomly along all or part of a desaturase coding sequence, such as by saturation mutagenesis, and the resultant mutants can be screened for desaturase biological activity to identify mutants that retain activity. Following mutagenesis of SEQ ID NO: 1 or 3, the encoded protein can be expressed recombinantly and the activity of the protein can be determined.

In a preferred embodiment, a mutant desaturase protein can be assayed for the ability to (i) interact with a desaturase substrate or target molecule (e.g., an intermediate fatty acid); and/or (ii) form a double bond between carbon atoms in a desaturase substrate or target molecule.

II. Isolated Desaturase Proteins

One aspect of the invention pertains to isolated or recombinant desaturase proteins and polypeptides, and biologically active portions thereof. In one embodiment, native desaturase proteins can be isolated from cells or tissue sources by an appropriate purification scheme using standard protein purification techniques. In another embodiment, desaturase proteins are produced by recombinant DNA techniques. Alternative to recombinant expression, a desaturase protein or polypeptide can be synthesized chemically using standard peptide synthesis techniques.

An "isolated" or "purified" protein or biologically active portion thereof is substantially free of cellular material or other contaminating proteins from the cell or tissue source from which the desaturase protein is derived, or substantially free from chemical precursors or other chemicals when chemically synthesized. The language "substantially free of cellular material" includes preparations of desaturase protein in which the protein is separated from cellular components of the cells from which it is isolated or recombinantly produced. In one embodiment, the language "substantially free of cellular material" includes preparations of desaturase protein having less than about 80%, 70%, 60%, 50%, 40%, or 30% (by dry weight) of non-desaturase protein (also referred to herein as a "contaminating protein"), more preferably less than about 20% of non-desaturase protein, still more preferably less than about 10% of non-desaturase protein, and most preferably less than about 5% non-desaturase protein. When the desaturase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of desaturase protein in which the protein is separated from chemical precursors or other chemicals which are involved in the synthesis of the protein. In one embodiment, the language "substantially free of chemical precursors or other chemicals" includes preparations of desaturase protein having less than about 30% (by dry weight) of chemical precursors or non-desaturase chemicals, more preferably less than about 20% chemical precursors or non-desaturase chemicals, still more preferably less than about 10% chemical precursors or non-desaturase chemicals, and most preferably less than about 5% chemical precursors or non-desaturase chemicals. It should be understood that the proteins or this invention can also be in a form which is different than their corresponding naturally occurring proteins and/or which is still in association with at least some cellular components. For example, the protein can be associated with a cellular membrane.

As used herein, a "biologically active portion" of a desaturase protein includes a fragment of a desaturase protein which participates in an interaction between a desaturase molecule and a non-desaturase molecule (e.g., a desaturase substrate such as fatty acid). Biologically active portions of a desaturase protein include peptides comprising amino acid sequences sufficiently homologous to or derived from the desaturase amino acid sequences, e.g., the amino acid sequences shown in SEQ ID NO:2 or 4 which include sufficient amino acid residues to exhibit at least one activity of a desaturase protein. Typically, biologically active portions comprise a domain or motif with at least one activity of the desaturase protein, for example, the ability to (i) interact with a desaturase substrate or target molecule (e.g., a fatty acid such as a saturated fatty acid and an intermediate fatty acid) and/or (ii) form a double bond between carbon atoms in a desaturase substrate or target molecule. A biologically active portion of a desaturase protein can be a polypeptide which is, for example, 10, 11, 12, 13, 14, 15, 16, 17, 18, 19, 20, 25, 30, 35, 40, 45, 50, 75, 100, 125, 150, 175, 200, 250, 300, 350, 400 or 450 or more amino acids in length.

In one embodiment, a biologically active portion of a desaturase protein comprises a domain conserved among desaturases and known to participate in a desaturase activity. For example, at least one domain or motif conserved among the CpDesX or CpDes12 amino acid sequences can be incorporated within the biologically active fragments in order to preserve desaturase activity. Alternatively, at least one domain or motif conserved among the fatty acid desaturases from different organisms, as depicted in FIG. 3, can be incorporated within the biologically active fragments in order to preserve desaturase activity. Specifically, desaturases often possess at least one histidine motif, preferably about three histidine motifs. For example, biologically active portions may include at least one the following histidine motifs: HECGH (SEQ ID NO: 18) (amino acid residues 155-159 of SEQ ID NO:2 or 4), HXXHH (amino acid residues 191-195 of SEQ ID NO:2 or 4) and HVXHH (SEQ ID NO: 19) (amino acid residues 391-395 of SEQ ID NO:2 or 4), where X may comprise any suitable amino acid. Such histidine motifs are often found in microsomal desaturases. Moreover, other biologically active portions, in which other regions of the protein are deleted, can be prepared by recombinant techniques and evaluated for one or more of the functional activities of a native desaturase protein.

In a preferred embodiment, a desaturase protein has an amino acid sequence shown in SEQ ID NO:2 or 4. In other embodiments, the desaturase protein is substantially identical to SEQ ID NO:2 or 4 and retains the functional activity of the protein of SEQ ID NO:2 or 4, yet differs in amino acid sequence due to natural allelic variation or mutagenesis, as described in detail in subsection I above. In another embodiment, the desaturase protein is a protein which comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, 90%, 91%, 92%, 93%, or 94%, and even more preferably at least about 95%, 96%, 97%, 98%, 99% or more identical to SEQ ID NO:2 or 4.

In another embodiment, the invention features a desaturase protein which is encoded by a nucleic acid molecule consisting of a nucleotide sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, and even more preferably at least about 95%, 96%, 97%, 98%, 99% or more identical to a nucleotide sequence of SEQ ID NO: 1 or 3, or a complement thereof. This invention further features a desaturase protein which is encoded by a nucleic acid molecule consisting of a nucleotide sequence which hybridizes under stringent hybridization conditions to a complement of a nucleic acid molecule comprising the nucleotide sequence of SEQ ID NO: 1 or 3, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CpDesX amino acid sequence of SEQ ID NO:2 having 477 amino acid residues, at least 143, preferably at least 191, more preferably at least 238, even more preferably at least 286, and even more preferably at least 334, 382, or 429 amino acid residues are aligned; and when aligning a second sequence to the CpDes12 amino acid sequence of SEQ ID NO:4 having 476 amino acid residues, at least 143, preferably at least 190, more preferably at least 238, even more preferably at least 285, and even more preferably at least 333, 381, or 428 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.*, 4:11-17 (1988)) which has been incorporated into the ALIGN program (version 2.0 or version 2.0U), using a PAM 120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to desaturase nucleic acid molecules of the invention. BLAST protein searches can be performed with the XBLAST program, score=50, wordlength=3 to obtain amino acid sequences homologous to desaturase protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

III. Methods of Producing Unsaturated Fatty Acids

The present invention provides new and improved methods of producing unsaturated fatty acids, e.g., long chain polyunsaturated fatty acids (LCPUFA's) and unsaturated fatty acids such as GLA 18:3 (6,9,12), ALA 18:3 (9,12,15), SDA 18:4 (6,9,12,15), AA 20:4 (5,8,11,14), EPA 20:5 (5,8,11,14,17), DPA 22:5 (4,7,10,13,16), DHA 22:6 (4,7,10,13,16,19), 20:4 (8,11,14,17), 16:2 (9,12), 18:2 (9,12) and 16:3 (9,12,15).

A. Recombinant Cells and Methods for Culturing Cells

The present invention further features recombinant vectors that include nucleic acid sequences that encode the gene products as described herein, preferably CpDesX and CpDes12 gene products. The term recombinant vector includes a vector (e.g., plasmid) that has been altered, modified or engineered such that it contains greater, fewer or different nucleic acid sequences than those included in the native vector or plasmid. In one embodiment, a recombinant vector includes the nucleic acid sequence encoding at least one fatty acid desaturase enzyme operably linked to regulatory sequences. The phrase "operably linked to regulatory sequence(s)" means that the nucleotide sequence of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant vector is introduced into a cell). Exemplary vectors are described in further detail herein as well as in, for example, Frascotti et al., U.S. Pat. No. 5,721,137, the contents of which are incorporated herein by reference.

The term "regulatory sequence" includes nucleic acid sequences which affect (e.g., modulate or regulate) expression of other (non-regulatory) nucleic acid sequences. In one embodiment, a regulatory sequence is included in a recombinant vector in a similar or identical position and/or orientation relative to a particular gene of interest as is observed for the regulatory sequence and gene of interest as it appears in nature, e.g., in a native position and/or orientation. For example, a gene of interest (e.g., a CpDesX or CpDes12 gene) can be included in a recombinant vector operably linked to a regulatory sequence which accompanies or is adjacent to the gene in the natural organism (e.g., operably linked to "native" CpDesX or CpDes12 regulatory sequence (e.g., to the "native" CpDesX or CpDes12 promoter). Alternatively, a gene of interest (e.g., a CpDesX or CpDes12 gene) can be included in a recombinant vector operably linked to a regulatory sequence which accompanies or is adjacent to another (e.g., a different) gene in the natural organism. For example, a CpDesX or CpDes12 gene can be included in a vector operably linked to non-CpDesX or CpDes12 regulatory sequences. Alternatively, a gene of interest (e.g., a CpDesX or CpDes12 gene) can be included in a vector operably linked to a regulatory sequence from another organism. For example, regulatory sequences from other microbes (e.g., other bacterial regulatory sequences, bacteriophage regulatory sequences and the like) can be operably linked to a particular gene of interest.

Preferred regulatory sequences include promoters, enhancers, termination signals and other expression control elements (e.g., binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a cell (e.g., constitutive promoters and strong constitutive promoters), those which direct inducible expression of a nucleotide sequence in a cell (e.g., inducible promoters, for example, xylose inducible promoters) and those which attenuate or repress expression of a nucleotide sequence in a cell (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant vector of the present invention includes nucleic acid sequences that encode at least one gene product (e.g., CpDesX or CpDes12) operably linked to a promoter or promoter sequence.

In a particular embodiment, seed-specific promoters are utilized to enhance the production of the desired unsaturated fatty acid. For example, U.S. Patent Publication No. 2003-0159174, published Aug. 21, 2003, the entire contents of which are hereby expressly incorporated by reference herein, describes the use of particular seed-specific promoters including, for example, Conlinin, Conlinin 2 and LuFad3 from the genus *Linum*. One skilled in the art will appreciate that other promoters, for example, seed-specific promoters such as napin, may be utilized to modulate, for example, enhance, the expression of the desaturase nucleotide sequence.

In yet another embodiment, a recombinant vector of the present invention includes a terminator sequence or terminator sequences (e.g., transcription terminator sequences). The term "terminator sequences" includes regulatory sequences which serve to terminate transcription of mRNA. Terminator sequences (or tandem transcription terminators) can further serve to stabilize mRNA (e.g., by adding structure to mRNA), for example, against nucleases.

In yet another embodiment, a recombinant vector of the present invention includes antibiotic resistance sequences. The term "antibiotic resistance sequences" includes sequences which promote or confer resistance to antibiotics on the host organism. In one embodiment, the antibiotic resistance sequences are selected from the group consisting of cat (chloramphenicol resistance), tet (tetracycline resistance) sequences, erm (erythromycin resistance) sequences, neo (neomycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

The term "manipulated cell" includes a cell that has been engineered (e.g., genetically engineered) or modified such that the cell has at least one fatty acid desaturase, e.g., CpDesX or CpDes12, such that an unsaturated fatty acid is produced. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, for example, as compared to a corresponding wild-type or naturally occurring enzyme.

The term "overexpressed" or "overexpression" includes expression of a gene product (e.g., a fatty acid desaturase) at a level greater than that expressed prior to manipulation of the cell or in a comparable cell which has not been manipulated. In one embodiment, the cell can be genetically manipulated (e.g., genetically engineered) to overexpress a level of gene product greater than that expressed prior to manipulation of the cell or in a comparable cell which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including, but not limited to, use of antisense nucleic acid molecules, for example, to block expression of repressor proteins).

In another embodiment, the cell can be physically or environmentally manipulated to overexpress a level of gene product greater than that expressed prior to manipulation of the cell or in a comparable cell which has not been manipulated. For example, a cell can be treated with or cultured in the presence of an agent known or suspected to increase transcription of a particular gene and/or translation of a particular gene product such that transcription and/or translation are enhanced or increased. Alternatively, a cell can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell that encodes an enzyme in a biosynthetic pathway, such that the level or activity of the biosynthetic enzyme in the cell is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a cell arises from the particular phenomenon of cells in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to, removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including, but not limited to, use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" cell of the present invention has been genetically engineered to overexpress a plant-derived gene or gene product or an microorganismally-derived gene or gene product. The term "plant-derived," "microorganismally-derived," or "derived-from," for example, includes a gene which is naturally found in a microorganism or a plant, e.g., an oilseed plant, or a gene product (e.g., CpDesX or CpDes12) or which is encoded by a plant gene or a gene from a microorganism (e.g., encoded SEQ ID NO:1 or SEQ ID NO:3).

The methodologies of the present invention feature recombinant cells which overexpress at least one fatty acid desaturase. In one embodiment, a recombinant cell of the present invention has been genetically engineered to overexpress a *Claviceps purpurea* fatty acid desaturase (e.g., has been engineered to overexpress at least one fatty acid desaturase having the amino acid sequence of SEQ ID NO:2 or 4 or encoded by the nucleic acid sequence of SEQ ID NO:1 or 3).

In another embodiment, the invention features a cell (e.g., a microbial cell) that has been transformed with a vector comprising a fatty acid desaturase nucleic acid sequence (e.g., a fatty acid desaturase nucleic acid sequence as set forth in SEQ ID NO: 1 or 3).

Another aspect of the present invention features a method of modulating the production of fatty acids comprising culturing cells transformed by the nucleic acid molecules of the present invention (e.g., a desaturase) such that modulation of fatty acid production occurs (e.g., production of unsaturated fatty acids is enhanced). The method of culturing cells transformed by the nucleic acid molecules of the present invention (e.g., CpDesX or CpDes12) to modulate the production of fatty acids is referred to herein as "biotransformation." The biotransformation processes can utilize recombinant cells and/or desaturases described herein. The term "biotransformation process," also referred to herein as "bioconversion processes," includes biological processes which result in the production (e.g., transformation or conversion) of any compound (e.g., substrate, intermediate, or product) which is upstream of a fatty acid desaturase or a compound (e.g., substrate, intermediate, or product) which is downstream of a fatty acid desaturase, in particular, an unsaturated fatty acid. In one embodiment, the invention features a biotransformation process for the production of an unsaturated fatty acid comprising contacting a cell which overexpresses at least one fatty acid desaturase with at least one appropriate substrate under conditions such that an unsaturated fatty acid is produced and, optionally, recovering the fatty acid. In a preferred embodiment, the invention features a biotransformation process for the production of unsaturated fatty acids comprising contacting a cell which overexpresses CpDesX or CpDes12 with an appropriate substrate (e.g., an intermediate fatty acid) under conditions such that an unsaturated fatty acid (e.g., DHA, SDA or GLA) is produced and, optionally, recovering the unsaturated fatty acid. Conditions under which an unsaturated fatty acid is produced can include any conditions which result in the desired production of an unsaturated fatty acid.

The cell(s) and/or enzymes used in the biotransformation reactions are in a form allowing them to perform their intended function (e.g., producing a desired fatty acids). The cells can be whole cells, or can be only those portions of the cells necessary to obtain the desired end result. The cells can be suspended (e.g., in an appropriate solution such as buffered solutions or media), rinsed (e.g., rinsed free of media from culturing the cell), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall). The type of cell can be any cell capable of being used within the methods of the invention, e.g., plant, animal, or microbial cells.

The type of cell can be any cell capable of being used within the methods of the invention, e.g., plant, animal, or microbial cells, preferably a plant or microbial cell. In one embodiment, the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacao*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*. In another embodiment, the cell is *Brassica juncea*. U.S. Patent Publication No. 2003-0159174, published Aug. 21, 2003, the entire contents of which are hereby expressly incorporated by reference herein, provides extensive teaching on the transformation of plant cells to optimize production of a desired end product.

In yet another embodiment, the cell is a microbial cell, for example, *Candida, Cryptococcus, Lipomyces, Rhodosporidium, Yarrowia, Thraustochytrium, Pythium irregulare, Schizochytrium* and *Crythecodinium*. One skilled in the art will appreciate that other microbial cells can be used in accordance with the methods provided herein, for example, for the production of a desaturated fatty acid.

An important aspect of the present invention involves growing the recombinant plant or culturing the recombinant microorganisms described herein, such that a desired compound (e.g., a desired unsaturated fatty acid) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism (e.g., carbon sources or carbon substrate, for example complex carbohydrates such as bean or grain meal, starches, sugars, sugar alcohols, hydrocarbons, oils, fats, fatty acids, organic acids and alcohols; nitrogen sources, for example, vegetable proteins, peptones, peptides and amino acids derived from grains, beans and tubers, proteins, peptides and amino acids derived form animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., an unsaturated fatty acid). In one embodiment, microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., an unsaturated fatty acid). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, plants or microorganisms of the present invention can be cultured under controlled temperatures. The term "controlled temperature" includes any temperature which results in production of the desired product (e.g., an unsaturated fatty acid). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., an unsaturated fatty acid). A variety of such processes have been developed and are well-known in the art.

The phrase "culturing under conditions such that a desired compound (e.g., an unsaturated fatty acid, for example, DHA) is produced" includes maintaining and/or growing plants or microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a unsaturated fatty acid (e.g., DHA). Preferably, culturing is continued for a time sufficient to substantially reach maximal production of the unsaturated fatty acid. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of unsaturated fatty acids, for example, cells are cultured such that at least about 15 to 20 g/L of unsaturated fatty acids are produced, at least about 20 to 25 g/L unsaturated fatty acids are produced, at least about 25 to 30 g/L unsaturated fatty acids are produced, at least about 30 to 35 g/L unsaturated fatty acids are produced, at least about 35 to 40 g/L unsaturated fatty acids are produced (e.g., at least about 37 g/L unsaturated fatty acids) or at least about 40 to 50 g/L unsaturated fatty acids are produced. In yet another embodiment, microorganisms are cultured under conditions such that a preferred yield of unsaturated fatty acids, for example, a yield within a range set forth above, is produced in about 24 hours, in about 36 hours, in about 48 hours, in about 72 hours, or in about 96 hours.

In producing unsaturated fatty acids, it may further be desirable to culture cells of the present invention in the presence of supplemental fatty acid biosynthetic substrates. The term "supplemental fatty acid biosynthetic substrate" includes an agent or compound which, when brought into contact with a cell or included in the culture medium of a cell, serves to enhance or increase unsaturated fatty acid biosynthesis. Supplemental fatty acid biosynthetic substrates of the present invention can be added in the form of a concentrated solution or suspension (e.g., in a suitable solvent such as water or buffer) or in the form of a solid (e.g., in the form of a powder). Moreover, supplemental fatty acid biosynthetic substrates of the present invention can be added as a single aliquot, continuously or intermittently over a given period of time.

The methodology of the present invention can further include a step of recovering a desired compound (e.g., an unsaturated fatty acid). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the unsaturated fatty acid of interest (e.g., DHA).

Preferably, a desired compound of the present invention is "extracted," "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound is an unsaturated fatty acid that has been derivatized to a salt, the compound is preferably further free (e.g., substantially free) of chemical contaminants associated with the formation of the salt. When the desired compound is an unsaturated fatty acid that has been derivatized to an alcohol, the compound is preferably further free (e.g., substantially free) of chemical contaminants associated with the formation of the alcohol.

In an alternative embodiment, the desired unsaturated fatty acid is not purified from the plant or microorganism, for example, when the plant or microorganism is biologically non-hazardous (e.g., safe). For example, the entire plant or culture (or culture supernatant) can be used as a source of product (e.g., crude product). In one embodiment, the plant or culture (or culture supernatant) supernatant is used without modification. In another embodiment, the plant or culture (or culture supernatant) is concentrated. In yet another embodiment, the plant or culture (or culture supernatant) is pulverized, dried, or lyophilized.

B. High Yield Production Methodologies

A particularly preferred embodiment of the present invention is a high yield production method for producing unsaturated fatty acids, e.g., DHA, comprising culturing a manipulated plant or microorganism under conditions such that the unsaturated fatty acid is produced at a significantly high yield. The phrase "high yield production method," for example, a high yield production method for producing a desired compound (e.g., for producing an unsaturated fatty acid) includes a method that results in production of the desired compound at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing unsaturated fatty acids that includes culturing a manipulated plant or microorganism under conditions such that an unsaturated fatty acid is produced at a level greater than 2 g/L. In another embodiment, the invention features a high yield production method of producing unsaturated fatty acids that includes culturing a manipulated plant or microorganism under conditions such that an unsaturated fatty acid is produced at a level greater than 10 g/L. In another embodiment, the invention features a high yield production method of producing unsaturated fatty acids that includes culturing a manipulated plant or microorganism under conditions such that an unsaturated fatty acid is produced at a level greater than 20 g/L. In yet another embodiment, the invention features a high yield production method of producing unsaturated fatty acids that includes culturing a manipulated plant or microorganism under conditions such that an unsaturated fatty acid is produced at a level greater than 30 g/L. In yet another embodiment, the invention features a high yield production method of producing unsaturated fatty acids that includes culturing a manipulated plant or microorganism under conditions such that an unsaturated fatty acid is produced at a level greater than 40 g/L.

The invention further features a high yield production method for producing a desired compound (e.g., for producing an unsaturated fatty acid) that involves culturing a manipulated plant or microorganism under conditions such that a sufficiently elevated level of compound is produced within a commercially desirable period of time. In an exemplary embodiment, the invention features a high yield production method of producing unsaturated fatty acids that includes culturing a manipulated plant or microorganism under conditions such that an unsaturated fatty acid is produced at a level greater than 15-20 g/L in 36 hours. In another embodiment, the invention features a high yield production method of producing unsaturated fatty acids that includes culturing a manipulated plant or microorganism under conditions such that an unsaturated fatty acid is produced at a level greater than 25-30 g/L in 48 hours. In another embodiment, the invention features a high yield production method of producing unsaturated fatty acids that includes culturing a manipulated plant or microorganism under conditions such that an unsaturated fatty acid is produced at a level greater than 35-40 g/L in 72 hours, for example, greater that 37 g/L in 72 hours. In another embodiment, the invention features a high yield production method of producing unsaturated fatty acids that includes culturing a manipulated plant or microorganism under conditions such that an unsaturated fatty acid is produced at a level greater than 30-40 g/L in 60 hours, for example, greater that 30, 35 or 40 g/L in 60 hours. Values and ranges included and/or intermediate within the ranges set forth herein are also intended to be within the scope of the present invention. For example, unsaturated fatty acid production at levels of at least 31, 32, 33, 34, 35, 36, 37, 38 and 39 g/L in 60 hours are intended to be included within the range of 30-40 g/L in 60 hours. In another example, ranges of 30-35 g/L or 35-40 g/L are intended to be included within the range of 30-40 g/L in 60 hours. Moreover, the skilled artisan will appreciate that culturing a manipulated microorganism to achieve a production level of, for example, "30-40 g/L in 60 hours" includes culturing the microorganism for additional time periods (e.g., time periods longer than 60 hours), optionally resulting in even higher yields of an unsaturated fatty acid being produced.

IV. Compositions

The desaturase nucleic acid molecules, proteins, and fragments thereof, of the invention can be used to produce unsaturated fatty acids which can be incorporated into compositions. Compositions of the present invention include, e.g., compositions for use as animal feed, compositions for use as neutraceuticals (e.g., dietary supplements), and pharmaceutical compositions suitable for administration. Such pharmaceutical compositions typically comprise an unsaturated fatty acid and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a LCPUFA, or a fragment thereof, produced by the nucleic acid and protein molecules of the present invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with a LCPUFA in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The pharmaceutical compositions can be included in a container, pack, or dispenser together with instructions for administration.

This invention is further illustrated by the following examples which should not be construed as limiting. The contents of all references, patents and published patent applications cited throughout this application, as well as the figures, are incorporated herein by reference.

EXAMPLES

Example 1

Organisms and Culture Conditions

*C. purpurea* (provided by Dr. Yu Chen, Department of Plant Science, University of Manitoba) was grown at 25° C.

for 14 days in medium C (Mantle and Nisbet, 1976). *S. cerevisiae* strain INVSc1 (Invitrogen, Carlsbad, Calif.) and AMY-2α[MATa, CYTb5, ole1(ΔBstEII)::LEU2, trp1-1, can1-100, ura3-1, ade2-1, HIS3] (Mitchell and Martin, 1995) were used as heterologous hosts to study substrate specificity and preference of the *C. purpurea* CpDesX and CpDes12 desaturase. Yeast cells were grown at 28° C. either in complex medium (YPD) or synthetic minimal medium (SD).

Example 2

Cloning of CpDesX and CpDes12 Desaturase cDNA

For reverse transcription-polymerase chain reaction (RT-PCR) experiments, the single stranded cDNA was synthesized by Superscript III reverse transcriptase (Invitrogen, Carlsbad, Calif.) using total RNA from sclerotium-forming mycelia of *C. purpurea*. The cDNA was then used as the template for the PCR reaction with two degenerate oligonucleotide primers, (DM34: 5'-GCICAYGARTGYGGICAY-SRIGCITT-3' (SEQ ID NO: 7) and DM36: 5'-TAIGT-DATIGCI ACIARCCARTGRTKIACCCA-3') (SEQ ID NO: 8). These primers were designed based on the conserved amino acid regions of delta12 desaturase and related proteins. The forward primer was in the first conserved histidine box and reverse primer was outside the histidine boxes, corresponding to the amino acid sequences AHECGH(G/Q)AF (SEQ ID NO: 9) and WV(N/H)HWLVAITY (SEQ ID NO: 10), respectively. To obtain the entire sequences of the cDNA, the 5' and 3' regions were amplified separately using the Marathon cDNA Amplification Kit (BD Biosciences Clontech, Mountain View, Calif.) according to the manufacturer's instructions. The primer DM40 (5'-CCACAGTGCGCAT-CACAAAGGA ACTGGAAA C-3') (SEQ ID NO: 11) was used to amplify the 3' region, and DM38 (5'-AGCCCAGC-CGA AACGGTTGCCAAGATAC-3') (SEQ ID NO: 12) and DM42 (5'-TGTTTGTCATCGAAAATAGGGCTG CGG-3') (SEQ ID NO: 13) were used to amplify the 5' region. The complete sequences including untranslated region were then amplified using specific primers DM47 (5'-GCCTGGAAT CGAAGCTACGTATCC-3') (SEQ ID NO: 14) and DM48 (5'-GACCGTCTTTAGCTACTTCGAGACAG-3') (SEQ ID NO: 15) by Pfx DNA polymerase (Invitrogen, Carlsbad, Calif.). The resulting bands were gel-purified, cloned into a pCR4-TOPO-TA cloning vector (Invitrogen, Carlsbad, Calif.) and sequenced.

Example 3

Expression of CpDesX and CpDes12 in *S. cerevisiae*

The coding region of the cDNA was amplified by PCR using the Pfx DNA polymerase (Invitrogen, Carlsbad, Calif.) with primers DM49 (5'-GCGAATTCAGGA TGGCTGC-TACCACTTCTGC-3') (SEQ ID NO: 16) and DM50 (5'-GC GAATTCCTACTGAGTTCTCAT CGAAATGG-3') (SEQ ID NO: 17) and cloned directly into pYES2.1 Topo-TA expression vector (Invitrogen, Carlsbad, Calif.) after Taq DNA polymerase treatment. The sequence of the insert of pDM14 was confirmed that is identical to the original cDNA and in the sense orientation relative to the GAL1 promoter.

Example 4

Yeast Transformation and Growth Conditions

*S. cerevisiae* strain INVSc1 or AMY2α was transformed with the construct using the S.C. EasyComp Transformation Kit (Invitrogen, Carlsbad, Calif.) with selection on uracil-deficient medium. For assessing the desaturase activity, recombinant yeast cells were grown to saturation in 25-ml cultures for 48 h at 28° C. on minimal medium (synthetic dropout) lacking uracil. The cultures were then washed and used to inoculate 25 ml of induction medium containing 2% galactose supplemented with or without 0.25 mM substrate fatty acids in the presence of 0.1% Tergitol (type Nonidet P-40). Cultures were incubated at 20° C. for 3 days. INVSc1 or AMY2α yeast containing the empty plasmid vector pYES2.1 was used as a negative control.

Example 5

Fatty Acid Analysis

For fatty acid analysis, yeast cells were pelleted by centrifugation, washed once with 0.1% tergitol and once with water. The fatty acids were converted to their methyl esters with 3 N methanolic HCl at 80° C. for 1 hour. After the addition of 1 mL of water, the sample was extracted twice with 2 mL of hexane. The hexane extract was combined and dried under $N_2$, and resuspended in 200 µL of hexane and analyzed on a Hewlett-Packard 5890A gas chromatograph equipped with a DB-23 column (30-m×0.25-mm) with 0.25-µm film thickness (J&W Scientific). The temperature program was isothermal 160° C. for 1 min, gradient 4° C./min to 240° C., and then isothermal at 240° C. for 10 min.

The position of newly introduced double bonds in desaturated fatty acid products was determined by GC-MS analysis of the 4,4-dimethyloxazoline (DMOX) derivatives as described previously (Qi et al., 2004). GC/MS analysis was accomplished using an Agilent 5973 mass selective detector coupled to an Agilent 6890N gas chromatograph using G1701DA MSD Chemstation software (for instrument control and data analysis) and equipped with a 30-m×0.25-mm DB-23 column with 0.25-µm film thickness (J&W Scientific). The chromatograph conditions included a split injection (20:1) onto the column using a helium flow of 0.4 ml/min, an initial temperature of 160° C. for 1 min, and a subsequent temperature ramp of 4° C./min to 240° C. The mass selective detector was run under standard electron impact conditions (70 eV), scanning an effective m/z range of 40-700 at 2.26 scans/s.

Example 6

Identification of a CpDesX and CpDes12 Desaturase cDNA from *C. purpurea*

*C. purpurea* was reported to be capable of producing ricinoleic acid (12OH-18:1-9) in the sclerotia, a pigmented and compact mass of mycelia (Morris et al., 1966). In a course of studying the biosynthetic mechanism of the hydroxyl fatty acid in this fungus, we identified several $\Delta^{12}$ desaturase-like genes from the tissues by using degenerate RT-PCR. The two primers were designed to target conserved regions of $\Delta^{12}$ desaturases from fungi, as previous reports have indicated that oleate hydroxlases from plants are highly homologous to plant $\Delta^{12}$ desaturases.

One of these genes (CpDesX) encodes a polypeptide of 477 amino acids in length and 53.1 kDa in molecular mass (FIG. 1). Another gene (CpDes12) codes for a 53 kDa protein of 476 amino acids in length (FIG. 2). Protein sequence comparison indicated that CpDesX and CpDes12 share 87% identity at the amino acid level (FIG. 3). Both sequences share sequence similarity to fungal $\Delta^{12}$ desaturases from *Aspergillus nidulans* (62% identity) (Calvo et al., 2001) and to plant $\Delta^{12}$ desaturases (Arondel et al., 1992) (40% amino acid identity).

Example 7

Functional Characterization of CpDesX in Yeast

Figures 5, 5A, 5B:
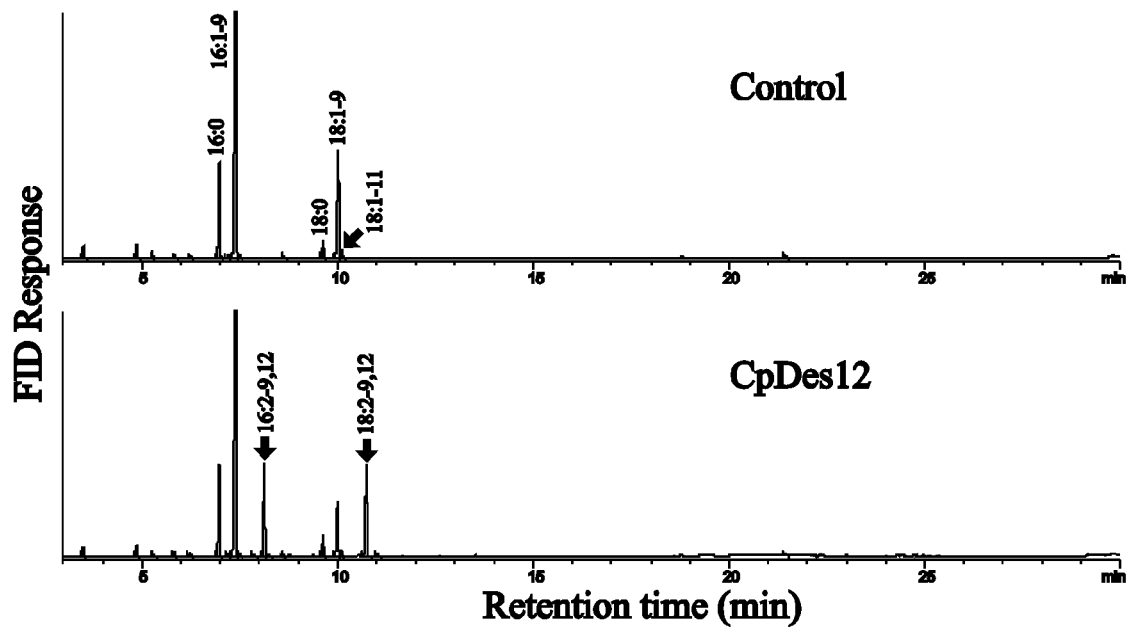
FIG. 5B is a gas chromatographic (GC) analysis of the expression of fatty acids in an experimental strain of yeast transformed with CpDes12 as compared to a control strain of yeast (FIG. 5A). The peaks 16:2 (9,12) and 18:2 (9,12) represent the presence of unsaturated fatty acids unique to the yeast strain transformed with CpDes12.

To determine the functionality of CpDes12 and CpDesX, the two cDNAs were introduced into yeast under guidance of a GAL1 promoter. Transformants containing CpDes12 produced two new fatty acids compared to the control yeast, which were identified as 16:2 (9c,12c) and 18:2 (9c,12c), indicating CpDes12 is a $\Delta 12$ desaturase from *C. purpurea* and could introduce a double bond at $\Delta^{12}$ position of both 16:1 (9c) and 18:1 (9c) (FIG. 5). Similarly, as compared to the control, transformants containing CpDesX produced five new fatty acids which were identified as 16:2 (9c,12t), 16:2 (9c,12c), 16:3 (9c,12c,15c), 18:2 (9c,12c) and 18:3 (9c,12c,15c), respectively (FIG. 4). This data indicates that CpDesX has multiple desaturase catalytic activities, including desaturation at $\Delta^{12}$, $\Delta^{15}$ and $\omega^3$ position of substrates.

Example 8

Substrate Specificity of CpDesX in Yeast

To unambiguously define the substrate specificity and regioselectivity of the desaturase, CpDesX was introduced into yeast mutant AMY2α, a $\Delta^9$ desaturase knockout strain that lacks ability to synthesize any monounsaturates. When fed with 18:1(9c), transformants produced two new fatty acids, 18:2 (9c,12c) and 18:3 (9c,12c,15c), indicating that CpDesX possesses $\Delta 12$ and $\Delta^{15}/\omega^3$ desaturase activities. Without wishing to be bound to any particular theory, it is believed that the CpDesX initially introduces a $\Delta^{12}$ double bond into the fed 18:1(9c), resulting in formation of 18:2 (9c,12c) which is subsequently desaturated by the $\Delta^{15}/\omega^3$ activity of the desaturase, forming 18:3 (9c,12c,15c) were produced. When fed with 16:1 (9t), no new product is detected. However, when fed with 16:1 (9c) transformants produced three new fatty acids identified as 16:2 (9c,12t), 16:2 (9c,12c) and 16:3 (9c,12c, 15c). The ratio of 16:2 (9c,12t) to 16:2 (9c,12c) produced is 0.6 with the latter predominating.

$\omega^3$ desaturases have been identified from worm (Meesapyodsuk et al., 2000a), fungi (Pereira et al., 2004) and plants (Meesapyodsuk et al., 2000b). Most of them are capable of introducing a $\omega^3$ double bond into $\omega^6$ polyunsaturates. To clarify the regiospecifcy of the $\omega^3$ desaturation activity of this desaturase, transformants were further presented with several $\omega^6$ polyunsaturated fatty acids such as LA, GLA, EDA (eicosadienoic acid), DGLA, AA, and DPA. Results indicated CpDesX could introduce an $\omega^3$ double bond into all $\omega^6$ fatty acids supplied except for DPAn-6, converting those $\omega^6$ polyunsaturates into their $\omega^3$ counterparts. Table 1 is the substrate preference of this desaturase on these substrates.

TABLE 1

$\omega^3$ conversion efficiency of yeast strain CpDesX/INVSc1 with exogenous $\omega^6$ substrates (Means and standard deviations based on four replicates are indicated. "% TFA" denotes weight percent of the total fatty acids.)

| Fatty acid supplement | Substrate Accumulation (% TFA) | Product Accumulation (% TFA) | conversion efficiency (%) |
|---|---|---|---|
| 18:2 (9c, 12c)(LA) | 3.4 ± 0.3 | 3.4 ± 0.2 | 50.2 ± 1.8 |
| 18:3 (6c, 9c, 12c) (GLA) | 6.1 ± 0.5 | 1.4 ± 0.1 | 19.0 ± 1.4 |
| 20:2 (11c, 14c) (EDA) | 2.5 ± 0.1 | 0.3 ± 0.0 | 11.9 ± 0.3 |
| 20:3 (8c, 11c, 14c) (DGLA) | 7.2 ± 0.9 | 0.9 ± 0.2 | 11.2 ± 0.6 |
| 20:4 (5c, 8c, 11c, 14c) (AA) | 3.0 ± 0.1 | 0.15 ± 0.0 | 4.6 ± 0.5 |

As shown in table 1, CpDesX acts on a wide range of substrates with a preference for LA, followed by GLA and then DGLA and AA.

Example 9

Expression of CpDesX in Plants

Figures 6, 6A, 6B:
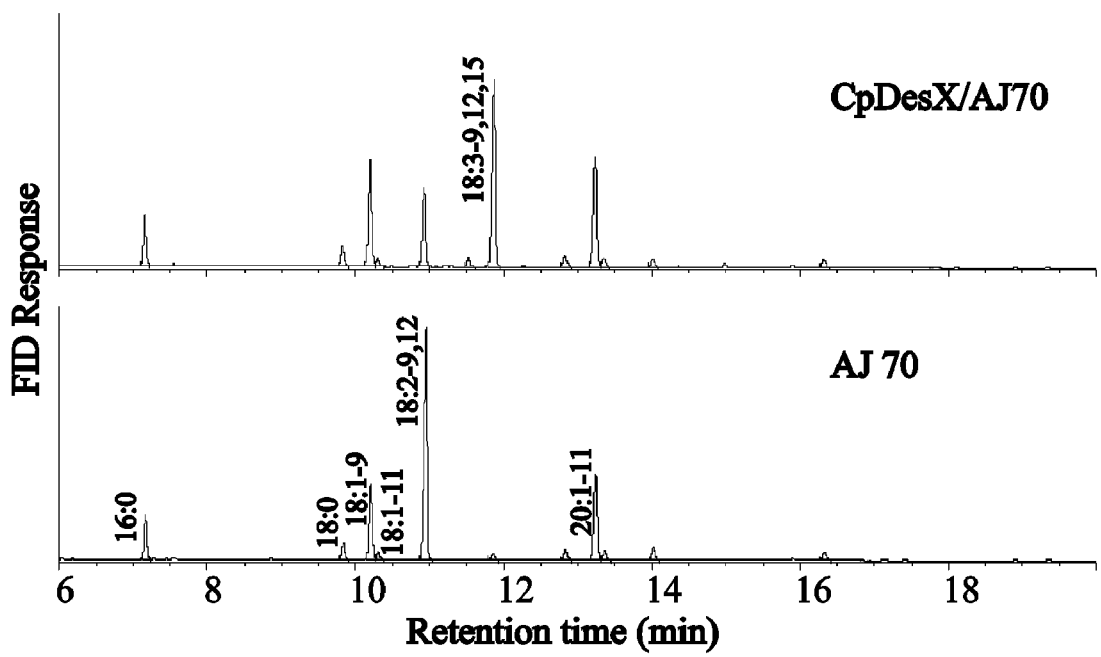
FIG. 6B is a gas chromatographic (GC) analysis of the expression of fatty acids in an experimental strain of *Arabidopsis thaliana* transformed with CpDesX as compared to a control strain of *Arabidopsis thaliana* (FIG. 6A). The peak representing the desaturated fatty acid 18:3 (9,12,15) is present in significantly higher amount in the experimental strain.

To examine the utility of CpDesX in the production of polyunsaturated fatty acids in plants, for example, for nutraceutical use, the CpDesX gene was expressed in *Arabidopsis thaliana* under the control of a seed-specific *Brassica napus* napin storage protein promoter. The binary vector for plant expression containing the candidate gene was introduced by the in-planta *Agrobacterium*-infiltration approach into *A. thaliana* AJ70, anAtfad3 mutant that is unable to synthesize 18:3 (9c,12c,13c) from 18:2 (9c,12c). Transgenic mature seeds were analyzed for the production of unusual fatty acids by gas chromatography. As depicted in FIG. 6, transgenic seeds containing the CpDesX gene produced substantial amount of linolenic acid. Indeed, 18:3 (9c,12c, 15c) constituted 33.3% of total fatty acid production in transgenic seeds as compared with the untransformed mutant in which 18 (9c,12c,15c) constituted less than 1% of total fatty acid production.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Boddupalli, S., and Somerville, C. (1998a). A bifunctional oleate 12-desaturase: desaturase from *Lesquerella fendleri*. Plant J. 13, 201-210.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Dyer, J. M., Chapital, D. C., Kuan, J. C., Mullen, R. T., Turner, C., McKeon, T. A., and Pepperman, A. B. (2002). Molecular analysis of a bifunctional fatty acid conjugase/desaturase from tung. Implications for the evolution of plant fatty acid diversity. Plant Physiol 130, 2027-2038.

Heilmann, I., Pidkowich, M. S., Girke, T., and Shanklin, J. (2004). Switching desaturase enzyme specificity by alternate subcellular targeting. Proc. Natl. Acad. Sci. U.S. A 101, 10266-10271.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-desaturase from *Mortierella alpina* by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbiol. 93, 321-334.

Meesapyodsuk, D., Reed, D. W., Savile, C. K., Buist, P. H., Ambrose, S. J., and Covello, P. S. (2000a). Characterization of the regiochemistry and cryptoregiochemistry of a *Caenorhabditis elegans* fatty acid desaturase (FAT-1) expressed in *Saccharomyces cerevisiae*. Biochemistry 39, 11948-11954.

Meesapyodsuk, D., Reed, D. W., Savile, C. K., Buist, P. H., Schafer, U. A., Ambrose, S. J., and Covello, P. S. (2000b). Substrate specificity, regioselectivity and cryptoregiochemistry of plant and animal omega-3 fatty acid desaturases. Biochem. Soc. Trans. 28, 632-635.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant. Microbe Interact. 15, 303-312.

Michaelson, L. V., Lazarus, C. M., Griffiths, G., Napier, J. A., and Stobart, A. K. (1998). Isolation of a Delta5-fatty acid desaturase gene from *Mortierella alpina*. J. Biol. Chem. 273, 19055-19059.

Mitchell, A. G. and Martin, C. E. (1995). A novel cytochrome b5-like domain is linked to the carboxyl terminus of the *Saccharomyces cerevisiae* delta-9 fatty acid desaturase. J. Biol. Chem. 270, 29766-29772.

Morris, L. J., Hall, S. W., and James, A. T. (1966). The biosynthesis of ricinoleic acid by *Claviceps purpurea*. Biochem. J. 100, 29C-30C.

Moto, K., Suzuki, M. G., Hull, J. J., Kurata, R., Takahashi, S., Yamamoto, M., Okano, K., Imai, K., Ando, T., and Matsumoto, S. (2004). Involvement of a bifunctional fatty-acyl desaturase in the biosynthesis of the silkmoth, *Bombyx mori*, sex pheromone. Proc. Natl. Acad. Sci. U.S. A 101, 8631-8636.

Okuley, J., Lightner, J., Feldmann, K., Yadav, N., Lark, E., and Browse, J. (1994). *Arabidopsis* FAD2 gene encodes the enzyme that is essential for polyunsaturated lipid synthesis. Plant Cell 6, 147-158.

Pereira, S. L., Huang, Y. S., Bobik, E. G., Kinney, A. J., Stecca, K. L., Packer, J. C., and Mukerji, P. (2004). A novel omega3-fatty acid desaturase involved in the biosynthesis of eicosapentaenoic acid. Biochem. J. 378, 665-671.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Qiu, X., Hong, H., and MacKenzie, S. L. (2001). Identification of a Delta 4 fatty acid desaturase from *Thraustochytrium* sp. involved in the biosynthesis of docosahexanoic acid by heterologous expression in *Saccharomyces cerevisiae* and *Brassica juncea*. J. Biol. Chem. 276, 31561-31566.

Sayanova, O., Smith, M. A., Lapinskas, P., Stobart, A. K., Dobson, G., Christie, W. W., Shewry, P. R., and Napier, J. A. (1997). Expression of a borage desaturase cDNA containing an N-terminal cytochrome b5 domain results in the accumulation of high levels of delta6-desaturated fatty acids in transgenic tobacco. Proc. Natl. Acad. Sci. U.S. A 94, 4211-4216.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Shanklin, J. and Whittle, E. (2003). Evidence linking the *Pseudomonas oleovorans* alkane omega-desaturase, an integral membrane diiron enzyme, and the fatty acid desaturase family. FEBS Lett. 545, 188-192.

Sperling, P., Lee, M., Girke, T., Zahringer, U., Stymne, S., and Heinz, E. (2000). A bifunctional delta-fatty acyl acetylenase/desaturase from the moss *Ceratodon purpureus*. A new member of the cytochrome b5 superfamily. Eur. J. Biochem. 267, 3801-3811.

Sperling, P., Ternes, P., Zank, T. K., and Heinz, E. (2003). The evolution of desaturases. Prostaglandins Leukot. Essent. Fatty Acids 68, 73-95.

Tudzynski, P., Correia, T., and Keller, U. (2001). Biotechnology and genetics of ergot alkaloids. Appl. Microbiol. Biotechnol. 57, 593-605.

SEQUENCE LISTING

```
<160> NUMBER OF SEQ ID NOS: 19

<210> SEQ ID NO 1
<211> LENGTH: 1434
<212> TYPE: DNA
<213> ORGANISM: Claviceps purpurea
<220> FEATURE:
<221> NAME/KEY: CDS
<222> LOCATION: (1)..(1431)

<400> SEQUENCE: 1 atg gct gct acc act tct gca atg tct aag gac gct gtt ctg cgg cgc      48
Met Ala Ala Thr Thr Ser Ala Met Ser Lys Asp Ala Val Leu Arg Arg
```

|     |     |     |     |     |     |     |     |     |     |     |     |     |     |     |     |      |
|---|---|---|---|---|---|---|---|---|---|---|---|---|---|---|---|---|
| act | gcg | gcc | gca | acg | act | gcc | atc | gat | cac | gag | tcg | tcg | acc | tct | gcc | 96 |
| Thr | Ala | Ala | Ala | Thr | Thr | Ala | Ile | Asp | His | Glu | Ser | Ser | Thr | Ser | Ala | |
| 1 | | | 20 | | 5 | | | 25 | | 10 | | | 30 | | 15 | | agt cca gcc gac tcg cct aga ctc tca gcc tcg tcc acg tcg ctt tcg   144
Ser Pro Ala Asp Ser Pro Arg Leu Ser Ala Ser Ser Thr Ser Leu Ser
            35                  40                  45 tcg ctt tct tct ctc gat gcg aag gac aag gac gac gag tat gcc ggc   192
Ser Leu Ser Ser Leu Asp Ala Lys Asp Lys Asp Asp Glu Tyr Ala Gly
     50                  55                  60 ctt ctt gac aca tac gga aac gcc ttc aca ccc ccc gac ttc act atc   240
Leu Leu Asp Thr Tyr Gly Asn Ala Phe Thr Pro Pro Asp Phe Thr Ile
 65                  70                  75                  80 aag gac atc cgt gat gcc ata ccc aag cat tgc ttc gaa cgc tct gcc   288
Lys Asp Ile Arg Asp Ala Ile Pro Lys His Cys Phe Glu Arg Ser Ala
                 85                  90                  95 atc aag gga tac gca tat att ctt cgc gac gtc gcc tgt ctt tct act   336
Ile Lys Gly Tyr Ala Tyr Ile Leu Arg Asp Val Ala Cys Leu Ser Thr
             100                 105                 110 acg ttc tac ctg ttc cac aac ttc gtg acg ccc gag aac gtc ccc tac   384
Thr Phe Tyr Leu Phe His Asn Phe Val Thr Pro Glu Asn Val Pro Tyr
         115                 120                 125 act ccc ctt cgt gtc ttt ctc tgg ggt gtt tac act gcc ctg caa ggt   432
Thr Pro Leu Arg Val Phe Leu Trp Gly Val Tyr Thr Ala Leu Gln Gly
     130                 135                 140 cta ttt gga act gga ctc tgg att att gcc cac gaa tgt ggc cac ggc   480
Leu Phe Gly Thr Gly Leu Trp Ile Ile Ala His Glu Cys Gly His Gly
145                 150                 155                 160 gcc ttc tct cct tca acc ttg acc aac gac ctt acc ggc tgg gtc ctt   528
Ala Phe Ser Pro Ser Thr Leu Thr Asn Asp Leu Thr Gly Trp Val Leu
                 165                 170                 175 cac tca gct ctc ctt gtt ccc tat ttc agc tgg aag ttt tcc cac agt   576
His Ser Ala Leu Leu Val Pro Tyr Phe Ser Trp Lys Phe Ser His Ser
             180                 185                 190 gcg cat cac aaa gga act gga aac atg gag cgc gac atg gct ttc ctt   624
Ala His His Lys Gly Thr Gly Asn Met Glu Arg Asp Met Ala Phe Leu
         195                 200                 205 ccc cgc aca cgt gcg cag tat gcc act cga ttt gga cgt gcg atg gat   672
Pro Arg Thr Arg Ala Gln Tyr Ala Thr Arg Phe Gly Arg Ala Met Asp
     210                 215                 220 caa ctt ggt gac ctt tgc gaa gag aca ccc att tac acg gct ggg ttc   720
Gln Leu Gly Asp Leu Cys Glu Glu Thr Pro Ile Tyr Thr Ala Gly Phe
225                 230                 235                 240 ttg gtt ttc cag cag ctc cta ggc tgg cct agc tat ctt ata gcg aac   768
Leu Val Phe Gln Gln Leu Leu Gly Trp Pro Ser Tyr Leu Ile Ala Asn
                 245                 250                 255 gtc aca ggt cac gac ctc cac gaa cgc cag cgt gag ggt cga ggt aag   816
Val Thr Gly His Asp Leu His Glu Arg Gln Arg Glu Gly Arg Gly Lys
             260                 265                 270 ggc aag aag aac ggt ttc ggg ggc acc gta aat cac ttt gat ccc cgc   864
Gly Lys Lys Asn Gly Phe Gly Gly Thr Val Asn His Phe Asp Pro Arg
         275                 280                 285 agc cct att ttc gat gac aaa cac gcc aag ttc att gtt ctc tct gac   912
Ser Pro Ile Phe Asp Asp Lys His Ala Lys Phe Ile Val Leu Ser Asp
     290                 295                 300 atc ggc ctg ggt ctt gct atc gct gct ctg gtg tat ctt ggc aac cgt   960
Ile Gly Leu Gly Leu Ala Ile Ala Ala Leu Val Tyr Leu Gly Asn Arg
305                 310                 315                 320 ttc ggc tgg gct aac gtg gct gtt tgg tat ttc gtg ccc tat ctt tgg   1008
Phe Gly Trp Ala Asn Val Ala Val Trp Tyr Phe Val Pro Tyr Leu Trp

```
                    325                 330                 335
gtg aat cac tgg atc gtt gcc atc acg ttc ctc cag cat acg gat cca      1056
Val Asn His Trp Ile Val Ala Ile Thr Phe Leu Gln His Thr Asp Pro
            340                 345                 350 act ctg ccg cat tac acc gcc gaa gag tgg aac ttt gtt cgc ggt gcc      1104
Thr Leu Pro His Tyr Thr Ala Glu Glu Trp Asn Phe Val Arg Gly Ala
        355                 360                 365 gct gct acc att gat cgc gag atg ggc ttc att ggc cgc cac ctt ttc      1152
Ala Ala Thr Ile Asp Arg Glu Met Gly Phe Ile Gly Arg His Leu Phe
370                 375                 380 cat ggc att gtc gag acc cat gtc ctc cat cac tat gtc agc tct ata      1200
His Gly Ile Val Glu Thr His Val Leu His His Tyr Val Ser Ser Ile
385                 390                 395                 400 ccg ttc tac aac gcg gac gaa gcc tcc gag gcc ata aaa ccg gtt atg      1248
Pro Phe Tyr Asn Ala Asp Glu Ala Ser Glu Ala Ile Lys Pro Val Met
            405                 410                 415 ggc aag cac tat cga tct gaa acc aaa gac gga ccc atg gga ttt atc      1296
Gly Lys His Tyr Arg Ser Glu Thr Lys Asp Gly Pro Met Gly Phe Ile
        420                 425                 430 cgc gct ctt tgg aag act gct cgc tgg tgc cag tgg gta gag cct agt      1344
Arg Ala Leu Trp Lys Thr Ala Arg Trp Cys Gln Trp Val Glu Pro Ser
    435                 440                 445 gcc gat gcg caa ggt gct gga gag ggc gtg ttg ttc ttc cgc aac cga      1392
Ala Asp Ala Gln Gly Ala Gly Glu Gly Val Leu Phe Phe Arg Asn Arg
450                 455                 460 aat ggt ctc ggc acg aaa ccc att tcg atg aga act cag tag              1434
Asn Gly Leu Gly Thr Lys Pro Ile Ser Met Arg Thr Gln
465                 470                 475

<210> SEQ ID NO 2
<211> LENGTH: 477
<212> TYPE: PRT
<213> ORGANISM: Claviceps purpurea

<400> SEQUENCE: 2

Met Ala Ala Thr Thr Ser Ala Met Ser Lys Asp Ala Val Leu Arg

```
                    180                 185                 190
Ala His His Lys Gly Thr Gly Asn Met Glu Arg Asp Met Ala Phe Leu
            195                 200                 205

Pro Arg Thr Arg Ala Gln Tyr Ala Thr Arg Phe Gly Arg Ala Met Asp
210                 215                 220

Gln Leu Gly Asp Leu Cys Glu Glu Thr Pro Ile Tyr Thr Ala Gly Phe
225                 230                 235                 240

Leu Val Phe Gln Gln Leu Leu Gly Trp Pro Ser Tyr Leu Ile Ala Asn
                245                 250                 255

Val Thr Gly His Asp Leu His Glu Arg Gln Arg Glu Gly Arg Gly Lys
            260                 265                 270

Gly Lys Lys Asn Gly Phe Gly Gly Thr Val Asn His Phe Asp Pro Arg
        275                 280                 285

Ser Pro Ile Phe Asp Asp Lys His Ala Lys Phe Ile Val Leu Ser Asp
        290                 295                 300

Ile Gly Leu Gly Leu Ala Ile Ala Ala Leu Val Tyr Leu Gly Asn Arg
305                 310                 315                 320

Phe Gly Trp Ala Asn Val Ala Val Trp Tyr Phe Val Pro Tyr Leu Trp
                325                 330                 335

Val Asn His Trp Ile Val Ala Ile Thr Phe Leu Gln His Thr Asp Pro
            340                 345                 350

Thr Leu Pro His Tyr Thr Ala Glu Glu Trp Asn Phe Val Arg Gly Ala
        355                 360                 365

Ala Ala Thr Ile Asp Arg Glu Met Gly Phe Ile Gly Arg His Leu Phe
    370                 375                 380

His Gly Ile Val Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Met Gly Phe Ile
            420                 425                 430

Arg Ala Leu Trp Lys Thr Ala Arg Trp Cys Gln Trp Val Glu Pro Ser
        435                 440                 445

Ala Asp Ala Gln Gly Ala Gly Glu Gly Val Leu Phe Phe Arg Asn Arg
450                 455                 460

Asn Gly Leu Gly Thr Lys Pro Ile Ser Met Arg Thr Gln
465                 470                 475

<210> SEQ ID NO 3
<211> LENGTH: 1431
<212> TYPE: DNA
<213> ORGANISM: Claviceps purpurea
<220> FEATURE:
<221> NAME/KEY: CDS
<222> LOCATION: (1)..(1428)

<400> SEQUENCE: 3 atg gct gct gct acc t

```
                    Ser Leu Ser Ser Leu Asp Ala Asn Asp Lys Lys Asp Glu Tyr Ala Gly
                        50                  55                  60 ctg ctt gac aca tac gga aac gcc ttc aca ccc ccc gac ttt acc atc            240
Leu Leu Asp Thr Tyr Gly Asn Ala Phe Thr Pro Pro Asp Phe Thr Ile
 65                  70                  75                  80 aag gac atc cgc gat gcc att ccc aag cat tgc tac gaa cgc tct gcc            288
Lys Asp Ile Arg Asp Ala Ile Pro Lys His Cys Tyr Glu Arg Ser Ala
                     85                  90                  95 ctc aaa ggc tac gga tac att ctt cgc gac atc gcc tgt ctt tcg acc            336
Leu Lys Gly Tyr Gly Tyr Ile Leu Arg Asp Ile Ala Cys Leu Ser Thr
                    100                 105                 110 acg ttc tac ctg ttc cac aac ttc gta acg ccg gag aat gtg ccg tcc            384
Thr Phe Tyr Leu Phe His Asn Phe Val Thr Pro Glu Asn Val Pro Ser
                115                 120                 125 act ccc ctt cga ttt gcg ctc tgg ggt att tac act gtc ctg caa ggt            432
Thr Pro Leu Arg Phe Ala Leu Trp Gly Ile Tyr Thr Val Leu Gln Gly
        130                 135                 140 ctt ttt gga acc gga ctt tgg gtc att gcc cac gaa tgt ggc cat ggt            480
Leu Phe Gly Thr Gly Leu Trp Val Ile Ala His Glu Cys Gly His Gly
145                 150                 155                 160 gca ttt tct ccg tcc acc ctc atc aac gac gtc act ggc tgg gtc ctt            528
Ala Phe Ser Pro Ser Thr Leu Ile Asn Asp Val Thr Gly Trp Val Leu
                    165                 170                 175 cac tca gct ctc ctc gtt cct tat ttc agc tgg aag ttt tcc cac agt            576
His Ser Ala Leu Leu Val Pro Tyr Phe Ser Trp Lys Phe Ser His Ser
                180                 185                 190 gct cat cac aag gcc acc gga cat atg gag cgc gac atg gtt ttt ctt            624
Ala His His Lys Ala Thr Gly His Met Glu Arg Asp Met Val Phe Leu
            195                 200                 205 ccc cga aca cgc gct caa cag gcc acc cga ctt ggg cgt gcg gtt gag            672
Pro Arg Thr Arg Ala Gln Gln Ala Thr Arg Leu Gly Arg Ala Val Glu
        210                 215                 220 gaa ctc ggc gat ctt tgc gag gag acg ccc att tac acg gcc ctg cac            720
Glu Leu Gly Asp Leu Cys Glu Glu Thr Pro Ile Tyr Thr Ala Leu His
225                 230                 235                 240 ttg gta ggc caa cag ctc atc ggt tgg ccc agc tac ctc atg gcc aac            768
Leu Val Gly Gln Gln Leu Ile Gly Trp Pro Ser Tyr Leu Met Ala Asn
                    245                 250                 255 gtc acg gga cac aat ttc cac gaa cgc cag cgg gag ggt cga ggc aaa            816
Val Thr Gly His Asn Phe His Glu Arg Gln Arg Glu Gly Arg Gly Lys
                260                 265                 270 ggc aag aag aac ggc ttc ggg ggc agc gtg aat cac ttt gat cct cgc            864
Gly Lys Lys Asn Gly Phe Gly Gly Ser Val Asn His Phe Asp Pro Arg
            275                 280                 285 agc cct att ttc gaa gcc cga cac gcc aag tac att gtt ctc tct gac            912
Ser Pro Ile Phe Glu Ala Arg His Ala Lys Tyr Ile Val Leu Ser Asp
        290                 295                 300 atc ggc ctg ggt ctt gcc atc gcc gct ttg gta tac ctc ggc aac cgg            960
Ile Gly Leu Gly Leu Ala Ile Ala Ala Leu Val Tyr Leu Gly Asn Arg
305                 310                 315                 320 ttc ggc tgg gct aac atg gct gtc tgg tac ttc ctt cct tat ctc tgg           1008
Phe Gly Trp Ala Asn Met Ala Val Trp Tyr Phe Leu Pro Tyr Leu Trp
                    325                 330                 335 gtg aac cac tgg ctc gtt gcc att acg ttc ctc cag cac acg gac cca           1056
Val Asn His Trp Leu Val Ala Ile Thr Phe Leu Gln His Thr Asp Pro
                340                 345                 350 act ctg cct cat tac aca gcc gaa gaa tgg aac tat gtt cgt gga gct           1104
Thr Leu Pro His Tyr Thr Ala Glu Glu Trp Asn Tyr Val Arg Gly Ala
            355                 360                 365 gct gct acc att gat cgc gag atg ggc ttc att ggc cgt cac ctt ctc           1152
```

```
cat ggc att att gag acc cat gtt ctc cac cac tat gtc agc tct att   1200
His Gly Ile Ile Glu Thr His Val Leu His His Tyr Val Ser Ser Ile
385                 390                 395                 400 ccc ttc tac aac gcc gac gaa gct tcc gag gcc atc aag cca gtc atg   1248
Pro Phe Tyr Asn Ala Asp Glu Ala Ser Glu Ala Ile Lys Pro Val Met
        405                 410                 415 ggc aag cac tat cga tcg gaa acc aaa gac ggc ccc gtc gga ttc atc   1296
Gly Lys His Tyr Arg Ser Glu Thr Lys Asp Gly Pro Val Gly Phe Ile
420                 425                 430 cgc gct ctt tgg aag act gct cgc tgg tgc cag tgg gta gag ccc agt   1344
Arg Ala Leu Trp Lys Thr Ala Arg Trp Cys Gln Trp Val Glu Pro Ser
            435                 440                 445 gcc gag gcc gag ggc gct ggc aag ggc gtc ttg ttc ttc cgc aac cga   1392
Ala Glu Ala Glu Gly Ala Gly Lys Gly Val Leu Phe Phe Arg Asn Arg
450                 455                 460 aac ggt ctg ggt aca aag ccc att tcg atg aag aat tag               1431
Asn Gly Leu Gly Thr Lys Pro Ile Ser Met Lys Asn
465                 470                 475

<210> SEQ ID NO 4
<211> LENGTH: 476
<212> TYPE: PRT
<213> ORGANISM: Claviceps purpurea

<400> SEQUENCE: 4

Met Ala Ala Ala Thr Ser Ala Met Pro Lys Asn Ser Val Leu Arg Arg
 1

```
Leu Val Gly Gln Gln Leu Ile Gly Trp Pro Ser Tyr Leu Met Ala Asn
                245                 250                 255

Val Thr Gly His Asn Phe His Glu Arg Gln Arg Glu Gly Arg Gly Lys
            260                 265                 270

Gly Lys Lys Asn Gly Phe Gly Ser Val Asn His Phe Asp Pro Arg
        275                 280                 285

Ser Pro Ile Phe Glu Ala Arg His Ala Lys Tyr Ile Val Leu Ser Asp
        290                 295                 300

Ile Gly Leu Gly Leu Ala Ile Ala Leu Val Tyr Leu Gly Asn Arg
305                 310                 315                 320

Phe Gly Trp Ala Asn Met Ala Val Trp Tyr Phe Leu Pro Tyr Leu Trp
                325                 330                 335

Val Asn His Trp Leu Val Ala Ile Thr Phe Leu Gln His Thr Asp Pro
            340                 345                 350

Thr Leu Pro His Tyr Thr Ala Glu Glu Trp Asn Tyr Val Arg Gly Ala
        355                 360                 365

Ala Ala Thr Ile Asp Arg Glu Met Gly Phe Ile Gly Arg His Leu Leu
        370                 375                 380

His Gly Ile Ile Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Val Gly Phe Ile
            420                 425                 430

Arg Ala Leu Trp Lys Thr Ala Arg Trp Cys Gln Trp Val Glu Pro Ser
                435                 440                 445

Ala Glu Ala Glu Gly Ala Gly Lys Gly Val Leu Phe Phe Arg Asn Arg
            450                 455                 460

Asn Gly Leu Gly Thr Lys Pro Ile Ser Met Lys Asn
465                 470                 475

<210> SEQ ID NO 5
<211> LENGTH: 383
<212> TYPE: PRT
<213> ORGANISM: Aspergillus nidulans

<400> SEQUENCE: 5

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser
        35                  40                  45

Ile Pro Arg Ser Phe Ser Tyr Leu Ile Ser Asp Ile Ile Ala Ser
    50                  55                  60

Cys Phe Tyr Tyr Val Ala Thr Asn Tyr Phe Ser Leu Leu Pro Gln Pro
65              70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140
```

```
His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380

<210> SEQ ID NO 6
<211> LENGTH: 420
<212> TYPE: PRT
<213> ORGANISM: Arabidopsis thaliana

<400> SEQUENCE: 6

Met Ala Ser Asp Ala Gly Lys Gly Asp Leu Gly Lys Met Leu Asp Thr
1               5                   10                  15

Tyr Gly Asn Glu Phe Lys Ile Pro Asp Tyr Thr Ile Lys Asp Ile Arg
            20                  25                  30

Asp Ala Ile Pro Ser His Cys Tyr Asn Arg Ser Ala Ile Arg Ser Leu
        35                  40                  45

Ser Tyr Val Phe Arg Asp Leu Ala Val Leu Ala Ser Val Phe Tyr Val
    50                  55                  60

Phe His Lys Tyr Val Thr Pro Glu Thr Val Pro Ser Tyr Pro Ala Arg
65                  70                  75                  80

Val Ala Leu Trp Thr Leu Tyr Thr Val Val Gln Gly Leu Phe Gly Thr
                85                  90                  95

Gly Ile Trp Val Leu Ala His Glu Cys Gly His Gln Ala Phe Ser Thr
            100                 105                 110

Ser Lys Val Leu Asn Asp Thr Val Gly Trp Ile Leu His Ser Ala Leu
        115                 120                 125

Leu Val Pro Tyr Phe Ser Trp Lys Ile Ser His Gly Lys His His Lys
    130                 135                 140
```

-continued

```
Ala Thr Gly Asn Leu Ala Arg Asp Met Val Phe Val Pro Lys Thr Arg
145                 150                 155                 160

Glu Val Tyr Ala Ser Arg Ile Lys Lys Thr Ile Tyr Asp Leu Asn Glu
            165                 170                 175

Val Met Glu Glu Thr Pro Leu Ala Thr Ala Thr His Ser Ile Leu Gln
        180                 185                 190

Gln Leu Phe Gly Trp Pro Leu Tyr Leu Leu Thr Asn Val Thr Gly His
    195                 200                 205

Asp Asn His Glu Arg Gln Pro Glu Gly Arg Gly Lys Gly Lys Arg Asn
210                 215                 220

Gly Tyr Phe Thr Gly Val Asn His Phe Asn Pro Asn Ser Pro Leu Phe
225                 230                 235                 240

Glu Ala Lys Asp Ala Lys Leu Ile Ile Leu Ser Asp Ile Gly Leu Ala
            245                 250                 255

Ile Thr Ala Ser Ile Leu Tyr Leu Ile Gly Ser Lys Phe Gly Trp Met
        260                 265                 270

Asn Leu Leu Val Trp Tyr Gly Ile Pro Tyr Leu Trp Val Asn His Trp
    275                 280                 285

Leu Val Ala Ile Thr Tyr Leu Gln His Thr Asp Pro Thr Leu Pro His
290                 295                 300

Tyr Gln Pro Glu Ser Trp Thr Phe Ala Arg Gly Ala Ala Ala Thr Ile
305                 310                 315                 320

Asp Arg Glu Phe Gly Phe Ile Gly Arg His Ile Leu His Gly Ile Ile
            325                 330                 335

Glu Thr His Val Leu His His Tyr Val Ser Thr Ile Pro Phe Tyr His
        340                 345                 350

Ala Asp Glu Ala Ser Glu Ala Ile Lys Lys Val Met Gly Ser His Tyr
    355                 360                 365

Arg Ser Glu Ala His Thr Gly Pro Leu Gly Phe Leu Lys Ala Leu Trp
370                 375                 380

Thr Ser Ala Arg Val Cys His Trp Val Glu Pro Thr Glu Gly Thr Lys
385                 390                 395                 400

Gly Glu Asn Ala Gly Val Leu Phe Phe Arg Asn Thr Asn Gly Ile Gly
            405                 410                 415

Val Pro Pro His
            420

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (15)
<223> OTHER INFORMATION: inosine
<220> FEATURE:
<221> NAME/KEY: modified_base
<222> LOCATION: (21)
<223> OTHER INFORMATION: inosine
<220> FEATURE:
<221> NAME/KEY: modified_base
<222> LOCATION: (24)
<223> OTHER INFORMATION: inosine

<400> SEQUENCE: 7
```

```
gcncaygart gyggncaysr ngcntt                                          26
```

```
<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (12)
<223> OTHER INFORMATION: inosine
<220> FEATURE:
<221> NAME/KEY: modified_base
<222> LOCATION: (15)
<223> OTHER INFORMATION: inosine
<220> FEATURE:
<221> NAME/KEY: modified_base
<222> LOCATION: (27)
<223> OTHER INFORMATION: inosine

<400> SEQUENCE: 8
tangtdatng cnacnarcca rtgrtknacc ca                                   32

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Gly or Gln

<400> SEQUENCE: 9

Ala His Glu Cys Gly His Xaa Ala Phe
  1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Asn or His

<400> SEQUENCE: 10

Trp Val Xaa His Trp Leu Val Ala Ile Thr Tyr
  1               5                  10

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
ccacagtgcg catcacaaag gaactggaaa c                                    31

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agcccagccg aaacggttgc caagatac                                        28

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgtttgtcat cgaaatagg gctgcgg                                          27

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcctggaatc gaagctacgt atcc                                            24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaccgtcttt agctacttcg agacag                                          26

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcgaattcag gatggctgct accacttctg c                                    31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
gcgaattcct actgagttct catcgaaatg g                                    31
```

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 18

His Glu Cys Gly His
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (3)
<223> OTHER INFORMATION: variable amino acid

<400> SEQUENCE: 19

His Val Xaa His His
 1               5

What is claimed:

1. An isolated nucleic acid molecule selected from the group consisting of:
   a) an isolated nucleic acid molecule comprising the nucleotide sequence of SEQ ID NO: 1, or the complement thereof;
   b) an isolated nucleic acid molecule which encodes a polypeptide comprising the amino acid sequence of SEQ ID NO: 2, or the complement thereof;
   c) an isolated nucleic acid molecule which encodes a polypeptide having at least 90% identity to the entire sequence of SEQ ID NO: 2, or the complement thereof; and
   d) an isolated nucleic acid molecule comprising a nucleotide sequence which is at least 90% identical to the entire nucleotide sequence of SEQ ID NO: 1, or the complement thereof.

2. The isolated nucleic acid molecule of claim 1, wherein said isolated nucleic acid molecule encodes a fatty acid desaturase protein having an activity of catalyzing the formation of a double bond in a fatty acid.

3. The isolated nucleic acid molecule of claim 1, wherein said isolated nucleic acid molecule encodes a fatty acid desaturase protein having an activity of catalyzing the formation of a double bond at position ω3, Δ12, or Δ15 of the fatty acid.

4. An isolated nucleic acid molecule comprising the isolated nucleic acid molecule of claim 1 and a nucleotide sequence encoding a heterologous polypeptide.

5. A vector comprising the isolated nucleic acid molecule of claim 1.

6. The vector of claim 5, which is an expression vector.

7. The vector of claim 5, wherein the isolated nucleic acid molecule is under the control of a seed-specific promoter.

8. The vector of claim 7, wherein the seed-specific promoter is selected from the group consisting of Conlinin 1, Conlinin 2, napin, and LuFad3.

9. An isolated host cell transformed with the expression vector of claim 6.

10. The isolated host cell of claim 9, wherein said isolated host cell is a plant cell or a microbial cell.

11. The isolated host cell of claim 10, wherein said plant cell is a cell obtained from an oilseed crop.

12. The isolated host cell of claim 11, wherein the oilseed crop is selected from the group consisting of flax (*Linum* sp.), rapeseed (*Brassica* sp.), soybean (Glycine and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, *lesquerella*, tallow tree, sheanuts, tungnuts, kapok fruit, poppy seed, jojoba seeds, and *perilla*.

13. The isolated host cell of claim 10, wherein the microbial cell is selected from the group consisting of *Candida, Cryptococcus, Lipomyces, Rhodosporidium, Yarrowia, Thraustochytrium, Pythium, Schizochytrium*, and *Crythecodinium*.

14. A method of producing a polypeptide comprising culturing the isolated host cell of claim 9 in an appropriate culture medium to, thereby, produce the polypeptide.

15. A method for producing an unsaturated fatty acid, comprising culturing the isolated host cell of claim 9 such that the unsaturated fatty acid is produced.

16. A method of producing a cell capable of generating an unsaturated fatty acid comprising introducing into a cell the isolated nucleic acid molecule of claim 1, wherein the isolated nucleic acid molecule encodes a desaturase having an activity of catalyzing the introduction of a double bond in a fatty acid.

17. A method of modulating the production of an unsaturated fatty acid comprising culturing the isolated host cell of claim 9, such that modulation of the production of an unsaturated fatty acid occurs.

18. A method for the large-scale production of an unsaturated fatty acid comprising culturing the isolated host cell of claim 9, such that the production of the unsaturated fatty acid occurs.

19. The method of claim 17, wherein the production of the unsaturated fatty acid is enhanced.

20. The method of any one of claims 15 and 16-18, wherein said method further comprises the step of recovering the unsaturated fatty acid from said culture.

21. The method of any one of claims 15, 16, 17 and 18, wherein said isolated host cell is a plant cell or a microbial cell.

22. The method of claim 21, wherein said plant cell is a cell obtained from an oilseed crop.

23. The method of claim 22, wherein the oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds, and *perilla*.

24. The method of claim 21, wherein the microbial cell is selected from the group consisting *Candida, Cryptococcus, Lipomyces, Rhodosporidium, Yarrowia, Thraustochytrium, Pythium, Schizochytrium,* and *Crythecodinium*.

25. The method of claim 15, 16 or 18, wherein expression of the isolated nucleic acid molecule results in modulation of production of said unsaturated fatty acid.

26. The method of any one of claims 15 and 16-18, wherein the unsaturated fatty acid is selected from the group consisting of GLA 18:3 (6,9,12), ALA 18:3 (9,12,15), SDA 18:4 (6,9,12,15), AA 20:4 (5,8,11,14), EPA 20:5 (5,8,11,14,17), DPA 22:5 (4,7,10,13,16), DHA 22:6 (4,7,10,13,16,19), 20:4 (8,11,14,17), 16:2 (9,12), 18:2 (9,12), and 16:3 (9,12,15).

27. A plant comprising the vector of claim 6.

28. A seed produced by a plant comprising the vector of claim 6, wherein the seed comprises said vector.

29. A composition comprising the seed of claim 28, wherein the composition is used in animal feed, a dietary supplement, or food.

30. A composition comprising the cell produced by the method of claim 16.

31. The composition of claim 30, wherein the composition is used in animal feed, a dietary supplement, or food.

32. The isolated nucleic acid molecule of claim 1, wherein the isolated nucleic acid molecule encodes a polypeptide having at least 95% identity to the entire sequence of SEQ ID NO: 2.

33. The isolated nucleic acid molecule of claim 1, wherein the isolated nucleic acid molecule comprising a nucleotide sequence which is at least 95% identical to the entire nucleotide sequence of SEQ ID NO: 1.

* * * * *